(12) United States Patent
Burnes et al.

(10) Patent No.: US 9,042,982 B2
(45) Date of Patent: *May 26, 2015

(54) ALGORITHM FOR THE AUTOMATIC DETERMINATION OF OPTIMAL AV AND VV INTERVALS

(75) Inventors: John E. Burnes, Andover, MN (US); Yong K. Cho, Maple Grove, MN (US); David Igel, Lino Lakes, MN (US); Luc R. Mongeon, Minneapolis, MN (US); John C. Rueter, Woodbury, MN (US); Harry Stone, White Bear Lake, MN (US); Jodi Zilinski, Brookfield, WI (US)

(73) Assignee: Medtronic, Inc., Minneapolis, MN (US)

( * ) Notice: Subject to any disclaimer, the term of this patent is extended or adjusted under 35 U.S.C. 154(b) by 79 days.

This patent is subject to a terminal disclaimer.

(21) Appl. No.: 13/400,381

(22) Filed: Feb. 20, 2012

(65) Prior Publication Data

US 2012/0150253 A1   Jun. 14, 2012

Related U.S. Application Data

(60) Division of application No. 11/751,250, filed on May 21, 2007, now Pat. No. 8,135,463, which is a continuation of application No. 10/135,912, filed on Apr. 29, 2002, now Pat. No. 7,228,174.

(51) Int. Cl.
*A61N 1/00* (2006.01)
*A61N 1/362* (2006.01)
(Continued)

(52) U.S. Cl.
CPC .......... *A61N 1/3627* (2013.01); *A61N 1/36521* (2013.01); *A61N 1/3682* (2013.01); *A61N 1/3684* (2013.01)

(58) Field of Classification Search
CPC ... A61N 1/362; A61N 1/3622; A61N 1/3627; A61N 1/36521; A61N 1/3684
USPC ........................................................ 607/4–28
See application file for complete search history.

(56) References Cited

U.S. PATENT DOCUMENTS 4,303,075 A   12/1981   Heilman et al.
4,686,987 A   8/1987   Salo et al.
(Continued)

FOREIGN PATENT DOCUMENTS

EP   1 350 539 A1   8/2003

OTHER PUBLICATIONS

Cazeau et al., PACE, vol. 17, Nov., 1994, Part II, pp. 1974-1979.
(Continued)

*Primary Examiner* — Scott Getzow
(74) *Attorney, Agent, or Firm* — Carol F. Barry

(57) ABSTRACT

Methods and devices for determining optimal Atrial to Ventricular (AV) pacing intervals and Ventricular to Ventricular (VV) delay intervals in order to optimize cardiac output. Impedance, preferably sub-threshold impedance, is measured across the heart at selected cardiac cycle times as a measure of chamber expansion or contraction. One embodiment measures impedance over a long AV interval to obtain the minimum impedance, indicative of maximum ventricular expansion, in order to set the AV interval. Another embodiment measures impedance change over a cycle and varies the AV pace interval in a binary search to converge on the AV interval causing maximum impedance change indicative of maximum ventricular output. Another method varies the right ventricle to left ventricle (VV) interval to converge on an impedance maximum indicative of minimum cardiac volume at end systole. Another embodiment varies the VV interval to maximize impedance change.

20 Claims, 17 Drawing Sheets

(51) Int. Cl.
*A61N 1/365* (2006.01)
*A61N 1/368* (2006.01)

(56) References Cited

U.S. PATENT DOCUMENTS

| | | | |
|---|---|---|---|
| 4,702,253 | A | 10/1987 | Nappholz et al. |
| 4,773,401 | A | 9/1988 | Citak et al. |
| 4,901,725 | A | 2/1990 | Nappholz et al. |
| 4,928,688 | A | 5/1990 | Mower |
| 5,179,946 | A | 1/1993 | Weiss |
| 5,201,808 | A | 4/1993 | Steinhaus et al. |
| 5,235,976 | A | 8/1993 | Spinelli |
| 5,292,340 | A | 3/1994 | Crosby et al. |
| 5,303,702 | A | 4/1994 | Bonnet et al. |
| 5,334,222 | A | 8/1994 | Salo et al. |
| 5,404,877 | A | 4/1995 | Nolan et al. |
| 5,501,702 | A | 3/1996 | Plicchi et al. |
| 5,507,785 | A | 4/1996 | Deno |
| 5,540,727 | A | 7/1996 | Tockman et al. |
| 5,584,868 | A | 12/1996 | Salo et al. |
| 5,609,610 | A | 3/1997 | Nappholz |
| 5,792,194 | A | 8/1998 | Mora |
| 5,792,195 | A | 8/1998 | Carlson et al. |
| 5,800,467 | A | 9/1998 | Park et al. |
| 5,824,019 | A | 10/1998 | Rueter et al. |
| 5,999,854 | A | 12/1999 | Deno et al. |
| 6,070,100 | A | 5/2000 | Bakels et al. |
| 6,134,472 | A | 10/2000 | Strandberg et al. |
| 2003/0083700 | A1 | 5/2003 | Hill |
| 2003/0105494 | A1 | 6/2003 | Kaye |
| 2003/0204212 | A1 | 10/2003 | Burnes et al. |

OTHER PUBLICATIONS

AHA 1991, Abstract from 64$^{th}$ Scientific Sessions, "Simultaneous Dual Atrium Pacing in High Degree Inter-Atrial Blocks: Hemodynamic Results," Daubert et al., No. 1804.

PACE, vol. 14, Apr. 1991, Part II, p. 648, "Prevention of Atrial Tachyarrythmias Related to Inter-Atrial Block by Permanent Atrial Resynchronization," Mabo et al., No. 122.

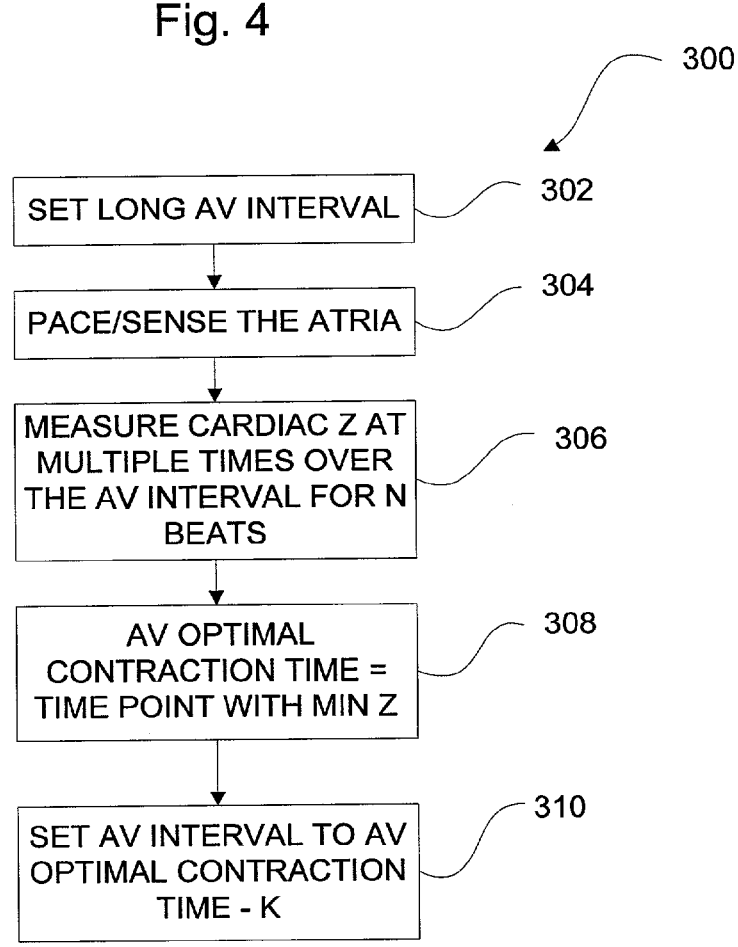

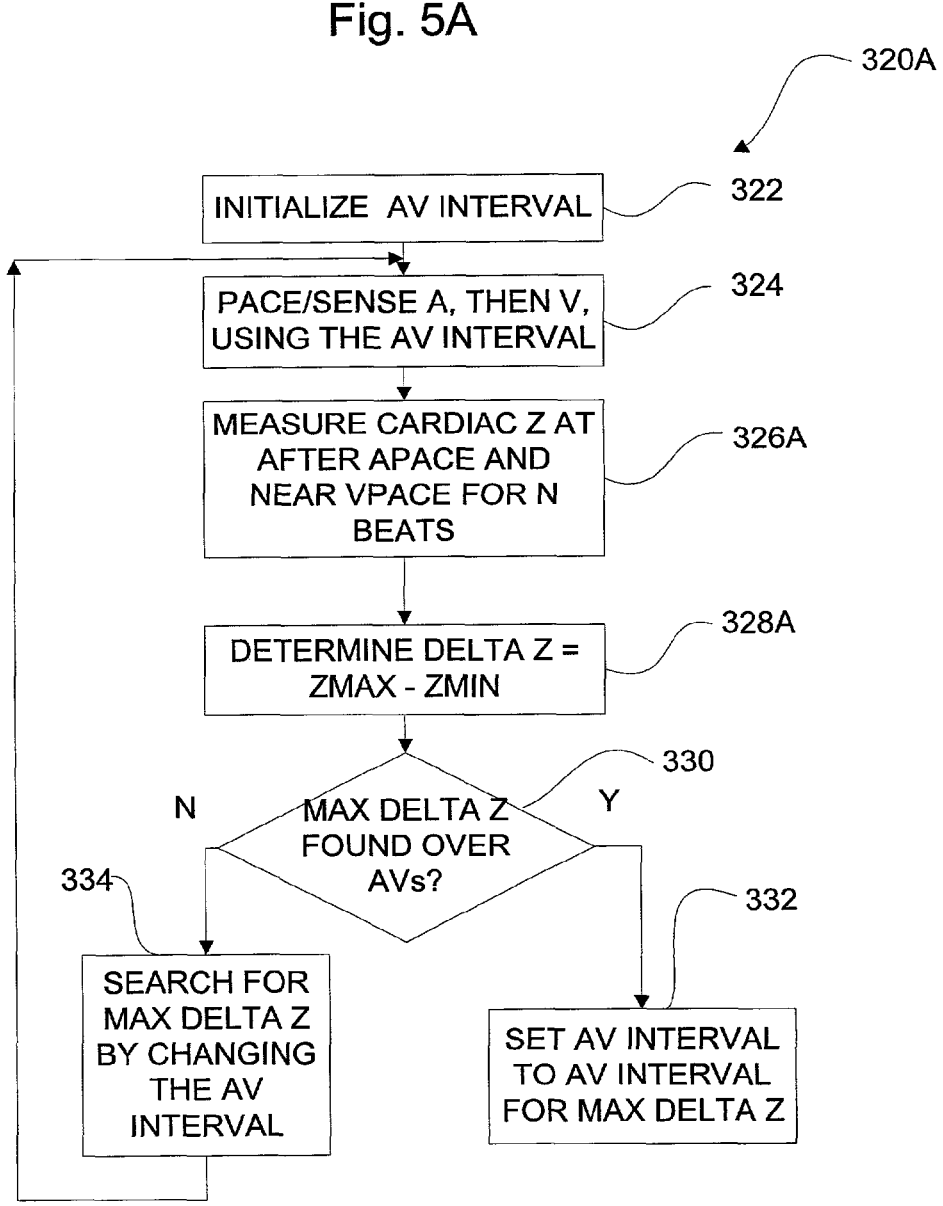

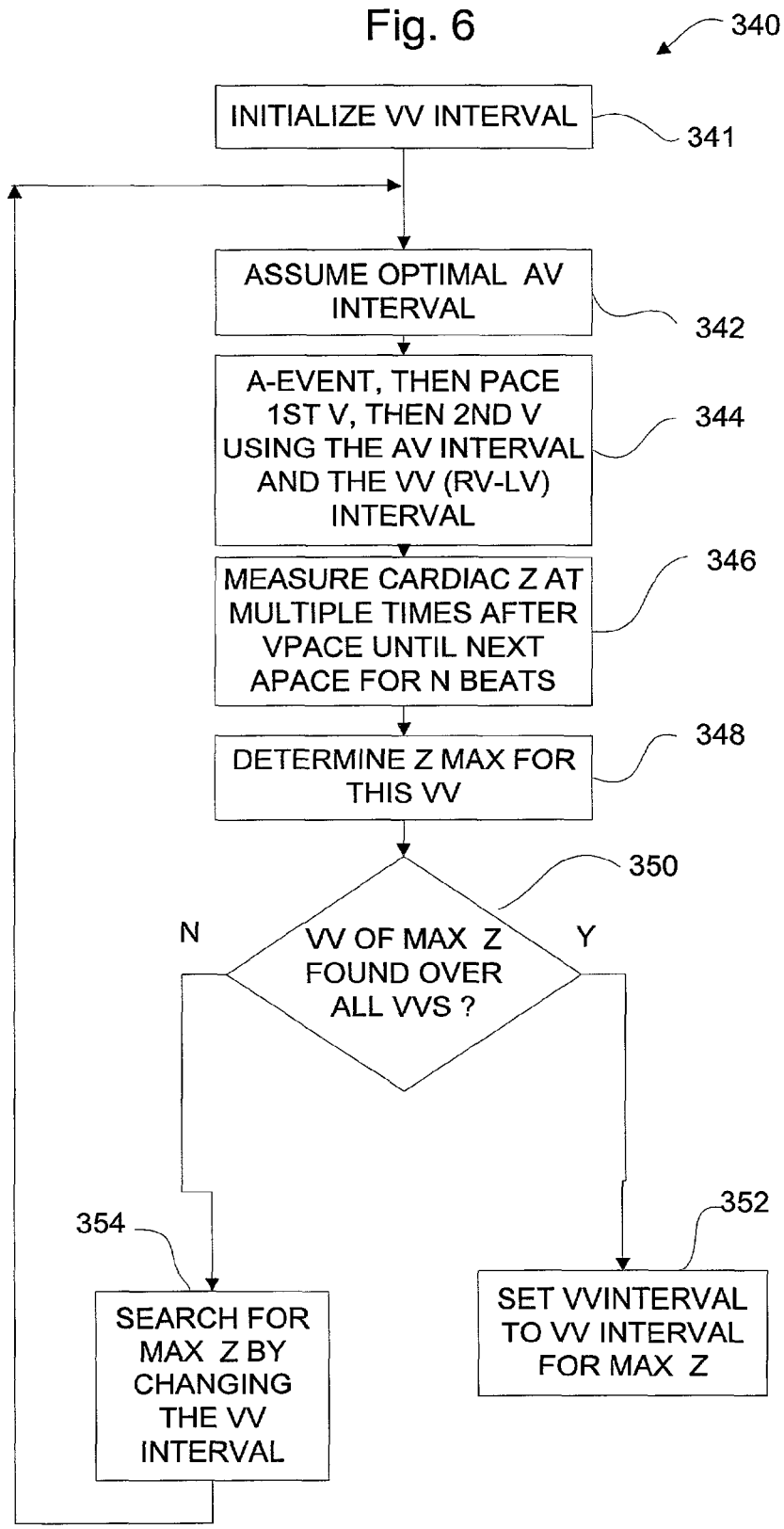

ALGORITHM FOR THE AUTOMATIC DETERMINATION OF OPTIMAL AV AND VV INTERVALS

RELATED APPLICATION

This application is a divisional of U.S. patent application Ser. No. 11/751,250, filed on May 21, 2007, entitled "ALGORITHM FOR THE AUTOMATIC DETERMINATION OF OPTIMAL AV AND VV INTERVALS" which is a continuation of U.S. patent application Ser. No. 10/135,912 filed on Apr. 29, 2002, entitled "ALGORITHM FOR THE AUTOMATIC DETERMINATION OF OPTIMAL AV AND VV INTERVALS", to Burnes et al., now U.S. Pat. No. 7,228,174 issued Jun. 5, 2007, incorporated herein by reference in its entirety.

FIELD OF THE INVENTION

The present invention is related generally to implantable cardiac pacemakers and cardioverter defibrillators. More specifically, the present invention includes apparatus and methods for using impedance measurements to set optimal pacing intervals.

BACKGROUND OF THE INVENTION

Congestive heart failure (CHF) is defined generally as the inability of the heart to deliver enough blood to the peripheral tissues to meet metabolic demands. Frequently CHF is associated with left heart dysfunction, but it can have a variety of other causes. For example, CHF patients may have any one of several different conduction defects. The natural electrical activation system through the heart involves sequential events starting with the sino-atrial (SA) node, and continuing through the preferred conduction pathways at the atrial level, followed by the atrio-ventricular (AV) node, Common Bundle of His, right and left bundle branches, and final distribution to the distal myocardial terminals via the Purkinje fiber network. A common type of intra-atrial conduction defect is known as intra-atrial block (IAB), a condition where the atrial activation is delayed in getting from the right atrium to the left atrium. In left bundle branch block and right bundle branch block, the activation signals are not conducted in a normal fashion along the left or right bundle branches respectively. Thus, in a patient with bundle branch block, the activation of the ventricle is slowed, and the QRS is seen to widen due to the increased time for the activation to traverse the conduction path.

CHF resulting from such conduction defects and/or other cardiomyopathies are the object of considerable research. It is known generally that four-chamber cardiac pacing and atrial synchronous bi-ventricular pacing can provide significant improvement for patients having atrial or ventricular mechanical dysynchrony resulting in dysfunction and symptoms of congestive heart failure.

The benefits of four-chamber pacing and atrial synchronous bi-ventricular pacing generally have been disclosed and published in the literature. Cazeau et al., PACE, Vol. 17, November.1994, Part II, pp. 1974-1979, disclosed investigations leading to the conclusion that four-chamber pacing was feasible, and that in patients with evidence of interventricular dyssynchrony, a better mechanical activation process can be obtained by resynchronizing depolarization of the right and left ventricles, and optimizing the AV sequence on both sides of the heart. In the patent literature, U.S. Pat. No. 4,928,688 is representative of a system for simultaneous left ventricular (LV) and right ventricular (RV) pacing; natural ventricular depolarizations are sensed in both chambers, if one chamber contracts but the other one does not within a window of up to 5-10 ms, then the non-contracting ventricular chamber is paced.

Further, similar to the advantages of substantially simultaneous or synchronous pacing of the two ventricles, there is an advantage to synchronous pacing of the left atrium and the right atrium for patients with IAB (inter-atrial block). In a normal heart, atrial activation initiates with the SA node. In a patient with IAB, the activation is slow being transferred over to the left atrium, and as a result the left atrium may be triggered to contract up to 90 ms later than the right atrium. It can be seen that if contractions in the left ventricle and the right ventricle are about the same time, then left AV synchrony is way off, with the left ventricle not having adequate time to fill up. The advantage of synchronous pacing of the two atria for patients with IAB is disclosed at AHA 1991, Abstract from 64th Scientific Sessions, "Simultaneous Dual Atrium Pacing in High Degree Inter-Atrial Blocks: Hemodynamic Results," Daubert et al., No. 1804

Further, it is known that patients with IAB are susceptible to retrograde activation of the left atrium, with resulting atrial tachycardia. Atrial resynchronization through pacing of the atria can be effective in treating the situation. PACE, Vol. 14, April 1991, Part II, p. 648, "Prevention of Atrial Tachyarrythmias Related to Inter-Atrial Block By Permanent Atrial Resynchronization," Mabo et al., No. 122. For patients with this condition, a criterion for pacing is to deliver a left atrial stimulus before the natural depolarization arrives in the left atrium.

In view of the published literature, it is observed that in CHF patients improved pump function can be achieved by increasing the filling time of the left ventricle, i.e., improving the left AV delay, and specifically the left heart mechanical AV delay (MAVD); decreasing mitral valve regurgitation, (back flow of blood into the atrium through the nearly closed valve) by triggering contraction of the left ventricle when it is maximally filled. More specifically, for a cardiac pacing system used for treating a CHF patient, the aim is to synchronize atrial and ventricular contractions through optimization of the left and right AV delays so as to properly fill the ventricles and provide maximal filling; and to activate the left ventricle as much as possible to contract in synchrony with the right ventricle. Correct programming of the AV interval is key for optimizing the filling of the ventricles, and optimizing ejection fraction, or cardiac output (CO). Particularly, the AV delay should be set to produce maximal filling of both ventricles during diastole and maximal emptying during systole.

Exact timing of left and right ventricular contraction is important for properly controlling pacing so as to optimize left ventricular output. Specifically, it is known that actual contraction of one ventricular chamber before the other has the effect of moving the septum so as to impair full contraction in the later activated chamber. Thus, while concurrent or simultaneous pacing of the left and right ventricle may achieve a significant improvement for CHF patients, pacing both left and right ventricles at the same time may not always be optimal. For example, if conduction paths in the left ventricle are impaired, delivering a pacing stimulus to the left ventricle at precisely the same time as to the right ventricle may nonetheless result in left ventricular contraction being slightly delayed with respect to the right ventricular contraction. Electrodes are now being positioned adjacent the left ventricle, and can be activated with sequential or simultaneous timing with respect to the right ventricle, resulting in varied timing and activation patterns. If the right and left ventricle are paced simultaneously this may not result in maximized pumping action, with the optimal pacing lead or lag between the ventricles being patient specific.

Echocardiography is sometimes used to set the AV interval in pacing devices. In this procedure, ultrasound is used to produce an echo cardiogram, followed by observation of the E and A waves. The AV interval can be clinically varied to optimize the E and A waves, so that the atrium is allowed to contract and fill the ventricles before the ventricle contracts. If the AV interval is too long, the valves are closed at ventricular contraction. If the AV interval is too short, LV filling does not receive the benefit of the atrial kick. Echocardiography is quite expensive, and can only be done infrequently, in a clinical setting. Quite frequently, the AV pacing intervals are set to a nominal AV interval, without echocardiography.

It is known to use impedance sensors in pacing systems, for obtaining information concerning cardiac function. For example, reference is made to U.S. Pat. No. 5,501,702, incorporated herein by reference, which discloses making impedance measurements from different electrode combinations. In such system, a plurality of pace/sense electrodes are disposed at respective locations, and different impedance measurements are made on a time/multiplexing basis. As set forth in the referenced patent, the measurement of the impedance present between two or more sensing locations is referred to "rheography." A rheographic, or impedance measurement involves delivering a constant current pulse between two "source" electrodes, such that the current is conducted through some region of the patient's tissue, and then measuring the voltage differential between two "recording" electrodes to determine the impedance therebetween, the voltage differential arising from the conduction of the current pulse through the tissue or fluid between the two recording electrodes. The referenced patent discloses using rheography for measuring changes in the patient's thoracic cavity; respiration rate; pre-ejection interval; stroke volume; and heart tissue contractility. It is also known to use this technique of four point impedance measurements, applied thorasically, for measuring small impedance changes during the cardiac cycle, and extracting the first time derivative of the impedance change, dZ/dt. It has been found that a substantially linear relation exists between peak dZ/dt and peak cardiac ejection rate, providing the basis for obtaining a measure of cardiac output. See also U.S. Pat. No. 4,303,075, disclosing a system for measuring impedance between a pair of electrodes connected to or in proximity with the heart, and processing the variations of sensed impedance to develop a measure of stroke volume. The AV delay is then adjusted in an effort to maximize the stroke volume.

Given the demonstrated desirability of cardiac resynchronization therapy (CRT), or bi-ventricular pacing, and the availability of techniques for sensing natural cardiac signals and mechanical events, there nonetheless remains a need to provide pacing intervals which are tuned for improving cardiac output, and in particular for improving left heart function. What would be particularly desirable is a method for also determining the optimal right side to left side pacing delay between the ventricles to obtain maximum cardiac output.

SUMMARY OF THE INVENTION

The present invention provides methods and devices for determining optimal atrial to ventricular (AV) pacing intervals and ventricular to ventricular (VV) delay intervals in order to optimize cardiac output. Impedance, preferably subthreshold impedance, is measured across the heart at selected cardiac cycle times as a measure of chamber expansion or contraction. The present methods can be used to particular advantage in four chamber and atrial synchronous bi-ventricular pacing devices used in cardiac resynchronization therapy (CRT). The methods can be implemented as executable logic or programs residing in implanted cardiac pacing devices.

A first method according to the present invention measures impedance over a long AV interval to obtain the minimum impedance, indicative of maximum ventricular expansion, in order to set the AV interval. The AV interval, as described in the present application, may extend from either A-sense or A-pace, with the term "A-event" being used to refer to either A-pace or A-sense. The AV interval, A-event to V-pace or V-sense, can first be set to a longer than normal interval in a clinical setting. In one method, the AV interval is set to about 300 ms in order to obtain a long period for impedance data gathering over one cycle. The impedance can be measured at multiple time points over the AV interval and the time point of minimum impedance determined. The minimum impedance is believed to correspond to the point of maximum expansion and filling of the ventricle, an optimal time for ventricle contraction for achieving maximum output. The time of impedance minimum can be used to set the AV pacing interval. Some methods reduce the time of minimum impedance by an offset to account for cardiac electromechanical delays. In some methods, the time of minimum impedance can be determined for several cycles and averaged. In yet another method, the impedance waveforms from several beats could be averaged together, after being aligned in time on the atrial or ventricular pacing pulse or sense, and the time of the minimum impedance determined from the averaged waveform.

A second method according to the present invention measures impedance change taken between times near the A-event and near the V-pace. The impedance change from A-event to V-pace is an impedance decrease as the ventricle fills with conductive blood. This method attempts to maximize the atrial contribution to ventricular filling by producing the largest absolute change in volume (delta Z) between the A-event and V-pace, through manipulation of the AV interval. The impedance data can be obtained from measurements taken shortly after the A-pace and near the V-pace. The AV interval can be varied in a binary search to converge on maximum impedance change indicative of maximum ventricular output. In some methods, only one or a small number of impedance measurements are taken after the A-pace, and shortly before, during, or shortly after the V-pace. The impedance change can be determined by subtracting the impedance taken near the V-pace from the impedance taken near the A-pace. The small number of carefully timed measurements can substantially reduce the power required to determine the impedance change.

In one method, a single impedance measurement is taken shortly after A-event and a single measurement taken near the V-pace. In some methods, the impedance change is measured for several heart beats at the same AV interval, and the average maximum impedance change over several heartbeats used. In yet another method, the impedance waveforms from several beats are averaged together, after being aligned on the atrial or ventricular pacing pulse or sense, and the maximum impedance change determined from the averaged waveform. The impedance change from ventricular expansion after atrial contraction can be maximized as a function of AV interval to maximize the atrial contribution to ventricular filling. The AV interval can be varied to bracket to maximum impedance change over several beats. In one method, a search algorithm is used to rapidly converge on the maximum impedance change from both time directions. In a preferred method, a binary search is used to converge on the maximum impedance change. The binary search can provide rapid convergence in few heart beats requiring little power consumption.

A third method according to the present invention measures impedance change taken between times shortly before, during, or shortly after the first V-pace until shortly before, during, or shortly after the next A-event. This measurement range will identify the cardiac cycle impedance maximum and minimum. This method attempts to maximize the change in ventricular volume and largest change in impedance by producing the greatest ventricular filling and maximal ventricular emptying over the ventricular ejection period through manipulation of the AV interval. The AV interval can be varied in a binary search to converge on maximum impedance change indicative of maximum ventricular output. In some methods, only one or a small number of impedance measurements are taken shortly before, during, or shortly after the first V-pace, with the V-pace measurement being used in place of the minimum impedance to calculate the impedance change for a cardiac cycle. The impedance near the V-pace is typically very low, if not the minimum, and can be used to eliminate finding the minimum. The impedance change can be determined by subtracting either the impedance taken near the V-pace, or the minimum impedance found, from the maximum impedance found between the V-pace and the A-event.

In some methods, the impedance change is measured for several heart beats at the same AV interval, and the average maximum impedance change over several heartbeats used. In yet another method, the impedance waveforms from several beats are averaged together, after being aligned on the atrial or ventricular pacing pulse or sense, and the maximum impedance change determined from the averaged waveform. The impedance change from expansion to contraction can be maximized as a function of AV interval to maximize the cardiac output. The AV interval can be varied to bracket the maximum impedance change over several beats. In one method, a search algorithm is used to rapidly converge on the maximum impedance change from both time directions. In a preferred method, a binary search is used to converge on the maximum impedance change. The binary search can provide rapid convergence in few heart beats requiring little power consumption.

A fourth method varies the right ventricle to left ventricle (VV) interval to converge on an impedance maximum indicative of minimum cardiac volume at end systole. This method attempts to maximize the change in ventricular volume and largest change in impedance by producing the greatest ventricular filling and maximal ventricular emptying over the ventricular ejection period through manipulation of the VV interval. The maximum impedance in a cycle is obtained as an indication of the minimum cardiac volume associated with end systole. The impedance measurements can be taken at multiple times after V-pace until next A-pace. The time difference between pacing the right and left ventricle, the ventricle to ventricle (VV) interval, can be varied to find the VV interval having the maximum impedance. The paced VV interval can be varied to bracket the maximum impedance over several heart beats. In one method, a search algorithm is used to rapidly converge on the paced VV interval having the maximum impedance. In a preferred method, a binary search is used to converge on the paced VV interval having the maximum impedance change. The binary search can provide rapid convergence in few heart beats. In some methods, the maximum impedance is measured for several heart beats at the same VV interval, and the average maximum impedance over several heartbeats used. In yet another method, the impedance waveforms from several beats is averaged together after being aligned on the atrial or ventricular pacing pulse or sense, and the maximum impedance determined from the averaged waveform.

A fifth method varies the VV interval to maximize impedance change. The maximum impedance change in a cycle is obtained as an indication of the maximum ventricular output. The impedance data can be obtained from measurements taken shortly after the V-pace until the next A-event. The time difference between pacing the right and left ventricle, or the ventricle to ventricle (VV) interval, can be varied to find the VV interval causing the maximum impedance change. The paced VV interval can be varied to bracket the VV interval causing the maximum impedance change. In one method, a search algorithm is used to rapidly converge on the paced VV interval having the maximum impedance change. In a preferred method, a binary search is used to converge on the paced VV interval having the maximum impedance change. In some methods, the impedance change is measured for several heart beats at the same VV interval, and the average maximum impedance change over several heartbeats used. In yet another method, the impedance waveforms from several beats are averaged together after being aligned on the atrial or ventricular pacing pulse or sense, and the maximum impedance change determined from the averaged waveform.

In some combined methods, the AV interval is optimized using one of the AV interval optimization methods according to the present invention. With the AV interval set, the VV interval can be optimized using one of the present invention methods. The pacing device can then be set to pace using the VV interval, causing the A-event to RV-pace and A-event to LV-pace interval to be either the same, lead, or lag each other. With the VV interval set, the AV interval can be re-optimized, this time using the just determined optimal VV interval.

Impedance measurements can be taken from pacing signals, but are preferably measured using sub-threshold stimulation signals. In some methods, the sub-threshold stimulation signals are stimulated Right Ventricular Ring to Left Ventricular Ring, and measured Right Ventricular Tip to Left Ventricular Tip. The impedance vector is preferably selected to cross the left and/or right ventricle, depending on the embodiment and available electrodes. Any suitable combination of stimulation and sensing electrodes may be used in obtaining the impedance measurement for use in the present invention.

The impedance measurement is often significantly changed by breathing. Impedance is effected greatly by electrode distance. Breathing changes the dimensions of the chest and the position of the heart. The impedance measurement is thus usually a composite impedance formed of a small amplitude, high frequency cardiac wave superimposed on a large amplitude, low frequency breathing wave. Several methods can be used to provide the AV and VV interval optimization methods with impedance data by taking into account the breathing impedance change contribution to the composite impedance signal.

In one method, a patient assumes a supine position in a clinical setting, stops moving, and is instructed to hold their breath by a physician. The patient has an implanted pacing unit implementing one or more methods of the present invention. Upon breath hold, the physician uses a programmer unit to signal the pacing device to measure impedance, preferably for a limited number of seconds or beats. The impedance may be effected by breath hold, but at a constant level. The pacing unit can then use the impedance data obtained to optimize an AV and/or VV interval.

In another method, the patient assumes a supine position, stops moving, and holds their breath. The implanted pacing device detects the combination of lack of movement (acceleration), and breath hold, and measures impedance for a period.

In still another method, preferably during a period of little movement, most preferably during sleep, the pacing device tracks the breathing cycle, through any means appropriate, including an impedance signal or accelerometer signal. Logic executing in the implanted device can time or "gate" the taking of impedance data to occur only near the inspiration peak or expiration nadir, preferably during the expiration nadir. Taking the impedance during these time regions, windows, or ranges of relatively little impedance change can effectively eliminate most of the impedance change due to breathing. In some embodiments, only one or two cardiac cycles per breath are measured for impedance.

In still another method, signal processing or filtering is used to remove the higher frequency, smaller amplitude cardiac impedance wave from the lower frequency, larger amplitude breathing wave. This method is preferably done during sleep, during periods of little movement and regular breathing.

DESCRIPTION OF THE DRAWINGS

FIG. 4 is a flow chart of a method for determining an optimal AV interval by maintaining a long AV interval and searching for a time point within the interval having a minimum impedance corresponding to a maximally filled ventricle;

FIG. 5A is a flow chart of a method for obtaining an optimum AV interval by intelligently varying the AV interval to search for the AV interval causing a maximum impedance change, measured from an A-event to a V-pace, corresponding to a maximum diastolic ventricular filling;

FIG. 6 is a flowchart of a method for obtaining an optimal inter-ventricular time delay by intelligently varying the inter-ventricular time delay and searching for a maximum impedance corresponding to a maximum contraction of the ventricles;

DETAILED DESCRIPTION OF THE PREFERRED EMBODIMENTS

Figure 1:
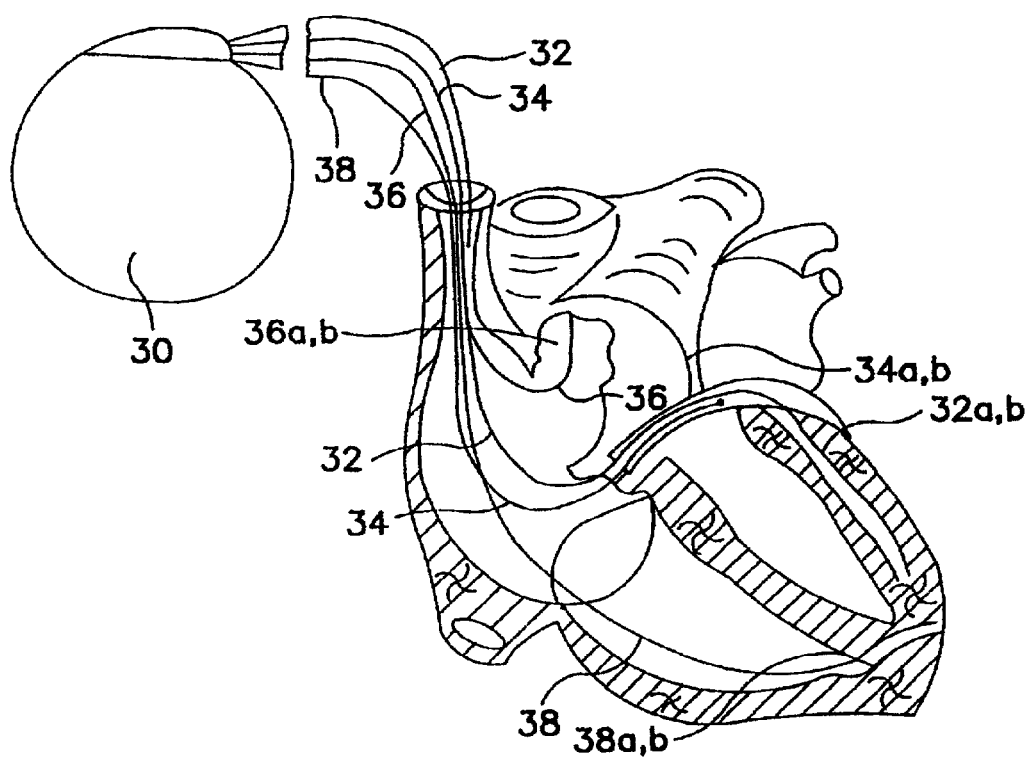
FIG. 1 is a schematic representation of a system in accordance with this invention, whereby four bipolar leads are provided, the leads being shown carrying bipolar electrodes positioned in each of the respective cardiac chambers.

Referring now to FIG. 1, there is shown a schematic representation of a four-chamber pacing system, illustrating four pacing leads providing bipolar electrodes positioned for pacing and sensing in each of the respective heart chambers, and also for impedance measurements. Pacing lead 38 is positioned conventionally such that its distal end is in the right ventricular apex position. It carries bipolar electrodes 38*a* and 38*b* adapted for pacing and sensing; additionally, these electrodes can also be used for impedance sensing as discussed below. Likewise, atrial lead 36 is positioned so that its distal end is positioned within the right atrium, with bipolar electrodes 36*a*, 36*b*. Lead 34 is passed through the right atrium, so that its distal end is positioned in the coronary sinus for pacing, sensing and impedance detection through electrodes 34*a, b*, as shown. Likewise, lead 32 is positioned via the coronary sinus a cardiac vein, e.g., the middle or great cardiac vein, so that distal electrodes 32*a* and 32*b* are positioned approximately as shown for pacing, sensing and impedance detection with respect to the left ventricle. The pacing leads are connected to pacemaker 30 in a conventional manner.

It is to be understood that the impedance measurements include "raw" measurements and "processed" measurements. Processed measurements include "average" measurements formed of the averages of more than one measurement, "filtered" measurements formed of filtered impedance measurements, "derivative" impedance measurements formed of the first or higher order derivatives of impedance measurements, "selected" impedance measurements formed of the highest or lowest impedance measurements from a set of impedance measurements, and "inverted" impedance measurements formed of inverted impedance measurements. The selected impedance measurements can be used to catch an impedance minimum or maximum from a time region including a small number, for example, 1 to 10, of impedance measurements. In embodiments having more than one pair of sensing electrodes, two or more sensing electrode impedance measurements can be added together to form an "augmented" impedance measurement. Similarly, one or more sensing electrode measurement can be subtracted from one or more other sensing electrode measurement to form a "subtracted" impedance measurement. Both the augmented and subtracted impedance measurements can provide valuable information gathered from the similarities or differences encountered by the stimulating current's path to the sensing electrodes. Unless noted otherwise, the impedance measurements used in all methods according to the present invention can be any of the aforementioned raw and processed impedance measurements and combinations thereof.

It also is to be understood that the system depicted here need not be limited to these lead positions, electrode sizes, and numbers of electrodes. Other embodiments of this system include multi-polar electrodes (3 or more electrodes on a single lead), defibrillation coils, and/or the pacemaker can. In some embodiments, the impedance measurement can be made between two or more stimulating electrodes and two or more sensing electrodes. which are not necessarily exclusive of each other. Specifically, some of the stimulating electrodes may also be sensing electrodes.

In some embodiments, the heart can be stimulated on one set of electrodes and recorded on two sets of electrodes. In one example, the heart is stimulated between the RV ring and the LV ring, and sensed by a first electrode pair between the RV tip and the RA tip, and also sensed by a second electrode pair between the LV tip and the RA tip.

Figure 2A:
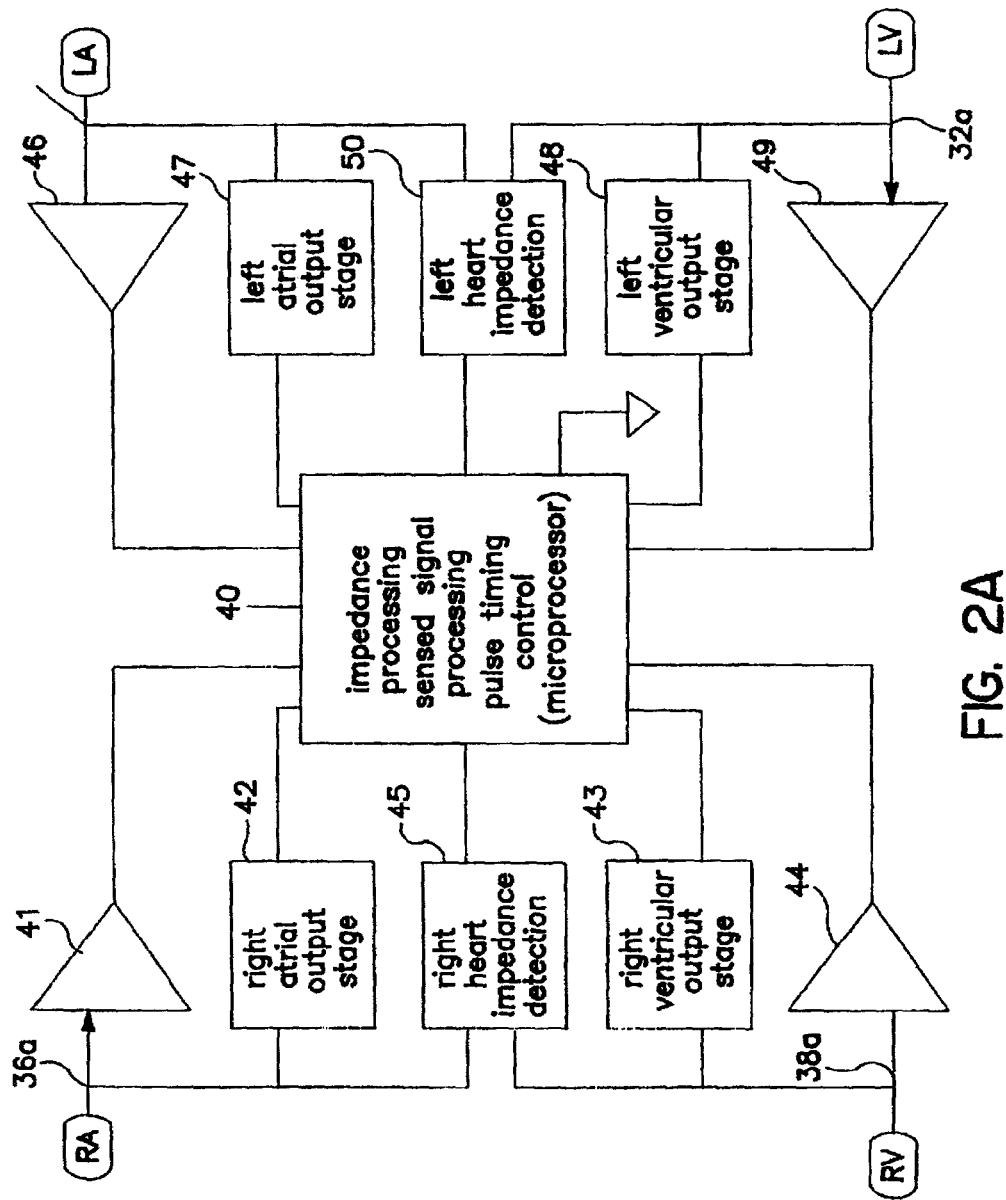
FIG. 2A is a block diagram of a four channel pacing system in accordance with this invention, for pacing and sensing in each ventricle, and for obtaining impedance signals from the left heart and the right heart.
Figure 2B:
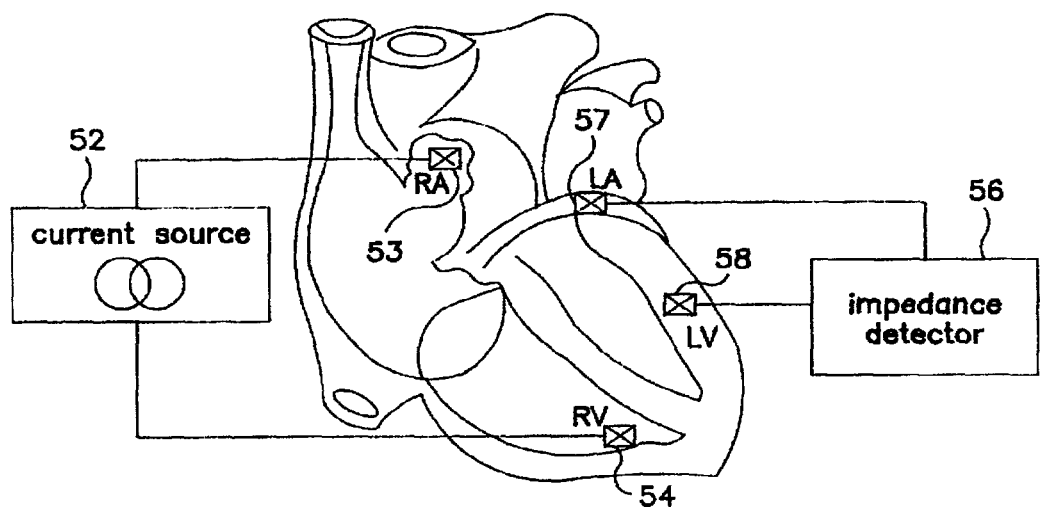
FIG. 2B is a schematic representation of an arrangement in accordance with this invention for detecting left ventricular impedance for determination of cardiac output.

Referring now to FIGS. 2A and 2B, there is shown a simplified block diagram of a four channel pacemaker in accordance with this invention, having the capability of impedance detection to sense chamber filing, and valve movement of the left and right ventricles. It is to be understood that the impedance detection scheme may be used to detect mechanical events, such as ventricular wall contraction or ventricular filling, in a known manner.

The system of FIG. 2A contains, in the pacemaker, a central processing block 40, indicated as including timing circuitry and a microprocessor, for carrying out logical steps in analyzing received signals, determining when pace pulses should be initiated, etc., in a well known fashion. Referring to the upper left-hand corner of the block diagram, there is shown signal amplifier circuitry 41, for receiving a signal from the right atrium. Electrode 36a is illustrated as providing an input, it being understood that the second input is received either from bipolar electrode 36b, or via an indifferent electrode (the pacemaker can) in the event of unipolar sensing. Likewise, a pulse generator 42, acting under control of block 40, generates right atrial pace pulses for delivery to electrode 36a and either electrode 36b or system ground. In a similar manner, right ventricular pace pulses are generated at output stage 43 and connected to electrode 38a, and sensed right ventricular signals are inputted to sense circuitry 44, the output of which is delivered to control block 40. Also illustrated is impedance detector 45, which receives inputs from electrodes 36a, 38a, for delivering information corresponding to ventricular volumes, which timing information is inputted into control block 40. Thus, the system enables pacing and sensing in each chamber, as well as impedance detection to provide an indication of degree of ventricular filling during diastole or emptying during systole.

Still referring to FIG. 2A, there are shown circuit components for the left atrium and the left ventricle. Output generator stage 47, under control of block 40, delivers left atrial pace pulses to stimulate the left atrium through electrode 34a and either electrode 34b or system ground. Inputs from the left atrial lead are connected through input circuitry 46, the output of which is connected through to control block 40. In a similar fashion, output stage 48, under control of block 40, provides left ventricular stimulus pace pulses which are delivered across electrode 32a and either electrode 32b or system ground; and left ventricular signals are sensed from lead 32 and inputted to input circuit 49, which provides an output to block 40 indicative of left ventricular signals. Also, dual inputs from the left atrial electrode 34a and left ventricular electrode 32a are inputted into left heart impedance detector 50, which provides timing pulses to block 40 indicative of ventricular volumes. With this arrangement, the pacemaker has the basic timing and cardiac signal information required to program delivery of pace pulses to respective heart chambers in accordance with this invention. Block 40 contains current generators for use in impedance detection; microprocessor or other logic and timing circuitry; and suitable memory for storing data and control routines.

Referring to FIG. 2B, there is shown a diagrammatic sketch of an arrangement for detecting left ventricular impedance change, which is processed in block 40 to obtain an indication of cardiac output. As shown, a current source 52 provides a constant current source across electrode 53 in the right atrium, which suitably can be electrode 36a; and right ventricular electrode 54, which suitably can be electrode 38a. The current source can be pulsed, or it can be multiplexed in a manner as discussed below. Impedance sensors 57 and 58 provide signals representative of impedance changes therebetween, the impedance being a function of blood volume, tissue between the electrodes, valve open/closed states, and distance. The outputs from electrodes 57, 58 is connected across impedance detector 56, which represents the microprocessor and/or other processing circuitry in block 40 for analyzing the impedance values and changes and making a determination of cardiac output.

Figure 3:
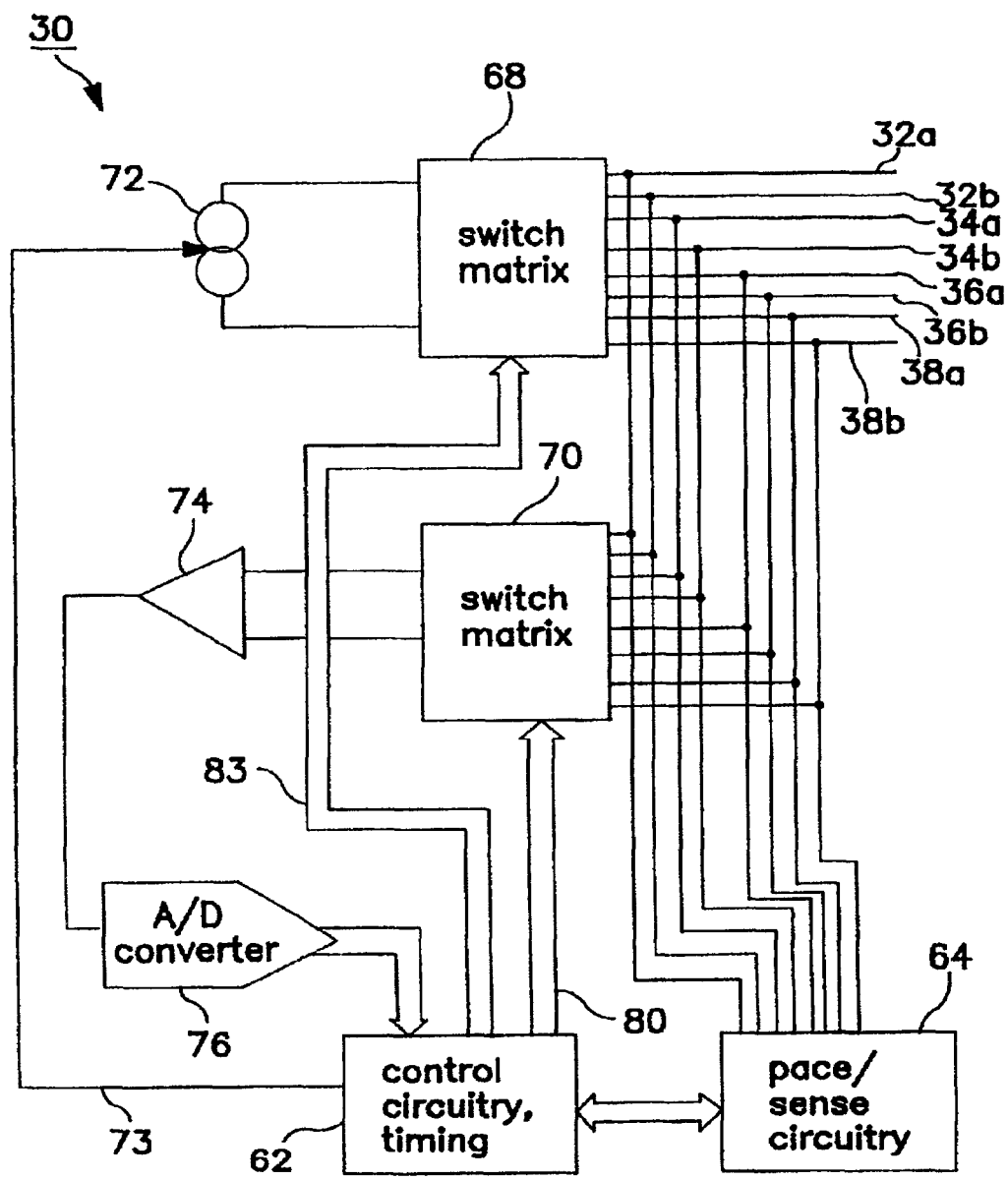
FIG. 3 is a block diagram of a four-chamber pacemaker with the ability to time multiplex impedance measurements, in accordance with this invention.

Referring now to FIG. 3, there is shown a block diagram of a pacemaker 30 in accordance with a preferred embodiment of this invention, for multiplexing connections to electrodes so as to provide for pacing and sensing between any of the implanted lead electrodes, defibrillation coils, or can, as well as for impedance determinations between respective different lead electrodes. Reference is made to U.S. Pat. No. 5,501,702, incorporated herein by reference, for a full discussion of this circuit, and in particular the multiplexing arrangement carried out by switch matrices 68, 70. The pacemaker 30 operates under control of circuitry 62, which may include a microprocessor or custom integrated circuitry, as well as associated memory, in a manner well known in the pacemaker art. Circuitry 62 provides for processing of data, and generation of timing signals as required. Control circuitry 62 is coupled to pace/sense circuitry 64, for processing of signals indicating the detection of electrical cardiac events, e.g., P-waves, R-waves, etc. sensed from conductors which connect electrically to electrodes 32a-38b, as shown. The aforementioned leads are also coupled to a first switch matrix 68 and a second switch matrix 70. Matrix 68 establishes a selectable interconnection between specific ones of the electrodes of leads 32, 34, 36 and 38, and the current source 72, is controlled by circuit 62. In a similar manner, switch matrix 70 establishes a selectable interconnection between lead conductors corresponding to selected electrodes, and impedance detection circuit 74, for the purpose of selecting impedance measurements.

With further reference to FIG. 3, current source 72 receives control signals on line 73 from circuitry 62, and is responsive thereto for delivering constant current rheography pulses onto lead conductors selected by switching matrix 68, which in turn is switched by signals on bus 83. Impedance detection circuit 74 is adapted to monitor the voltage between a selected pair of electrodes which pair is selectably coupled by operation of switch matrix 70 which in turn is switched by signals on bus 80. In this manner, circuit 74 determines the voltage, and hence the impedance, existing between two selected electrodes. The output of circuitry 74 is connected through A/D converter 76 to control circuitry 62, for processing of the impedance signals. The control of switch matrix 68 through signals on bus 78, and the control of switch matrix 70 through signals on bus 80, provides for multiplexing of different impedance signals.

It is to be understood that in the system arrangement of FIG. 3, pace/sense circuitry 64 may include separate stimulus pulse output stages for each channel, i.e., each of the four-chambers, each of which output stages is particularly adapted for generating signals of the programmed signal strength. Likewise, the sense circuitry of block 64 may contain a separate sense amplifier and processor circuitry for sensed signals from each chamber, such that sensing of respective wave portions, such as the P-wave, R-wave, T-wave, etc. from the right heart and the left heart, can be optimized. The pulse generator circuits and sense circuits as used herein are well known in the pacemaker art. In addition, other functions may be carried out by the control circuitry including standard pacemaker functions such as compiling of diagnostic data, mode switching, etc.

FIG. 4 illustrates an embodiment 300 for finding the time point of minimum impedance between an A-event and V-event. The time of minimal impedance can be used to set an optimal AV interval. Embodiment 300, and other AV and VV internal optimization methods disclosed in the present invention can be used in various settings, including a clinical setting with breath hold, a clinical setting with respiration tracking and gating, a clinical setting with respiration filtering, and ambulatory settings with breath hold, respiration tracking with gaiting, and respiration filtering. These settings can be used as a precondition for obtaining the impedance measurements discussed with respect to method 300, and, unless noted otherwise, other methods according to the present invention.

In Step 302, a long AV interval can be set. The long AV interval is preferably an AV interval longer than physiologically appropriate for the patient, for example two or three times longer. In a typical patient, the nominal AV interval may normally be about 100 milliseconds. One long AV interval can be about 300 or 200 milliseconds. In patients not being chronically paced, in a clinical setting, the implanted pacing device can be set to A-pace, then wait for the V sense. The long AV interval allows the implanted pacing device an expanded period of observation.

In step 304, the atria can be sensed or paced. In step 306, the cardiac impedance (Z) can be measured at multiple time points over the AV interval until the V-pace or V sense events occur. Step 306 can measure the impedance over numerous time points within the AV interval, searching for the time point having a minimum impedance. The minimum impedance will correspond to the time of maximum expansion of the ventricle, indicating the optimum time for contraction to occur. In some methods, step 306 takes measurements at a large number of time points over a single AV interval. In other embodiments, step 306 takes a large number of impedance measurements over several successive cardiac cycles with the same AV interval, to obtain an average impedance wave form over the AV interval. In yet another embodiment, a small number of impedance measurements, as low as one, can be taken over successive cardiac cycles with the same AV interval with the single or small number of impedance time points being intelligently timed to effectively search for the impedance minimum. The impedance minimum can be found by searching the wave form for a minimum, using methods well known to those skilled in the art. In one method, a complete wave form is completed for the AV interval, followed by searching the historical data for the minimum impedance. A binary search can be performed on the wave form data, or the slopes of wave form segments can be used to converge on the impedance minimum.

In step 308, the optimal AV contraction time can be set equal to the time point during the AV interval having the minimum impedance. In one embodiment, the implanted pacing device can have the AV pacing interval set equal to the time point having the minimal impedance, or the AV optimal contraction time itself. In a preferred embodiment, in step 310, the cardiac electrical-mechanical delay between the pace and the contraction is accounted for by offsetting the optimal contraction time with a constant interval, allowing the pace event to lead the optimal contraction time. In one embodiment, the offset is set to about 75 milliseconds. In another embodiment, the offset is set to between about 50 and 100 milliseconds. In still another embodiment, the offset is set to between about 25 and 200 milliseconds.

In some embodiments, the optimal AV interval thus obtained can be used as a base interval to be further acted upon in demand pacing algorithms. In one method, method 300 is executed at substantially regular intervals, but not at every heartbeat. In one embodiment, method 300 is executed about every hour. In this embodiment, the long AV interval is set for one or a small number of heartbeats, followed by the cardiac impedance measurements. In yet another embodiment, method 300 is executed when sleep is inferred from other indicators, for example, accelerometer readings and/or respiration readings.

The impedance measurement of embodiment 300 and the other methods discussed in the present application, can be measured as a vector across the best available leads present in the heart. In a bi-ventricular implanted pacing device, the impedance can be measured between a right ventricular electrode and a left ventricular electrode disposed in a cardiac vein. In one example, the impedance signal is stimulated between the left ventricular ring and the right ventricular ring and detected by the left ventricular tip and the right ventricular tip. The electrode pairs can be selected to maximize the impedance changes caused by the ventricular contractions and expansions. In another embodiment, having a ventricular lead, different electrodes disposed along the ventricular lead may be used to stimulate and sense the impedance vector.

FIG. 5A illustrates another embodiment 320A for optimizing the AV interval. While method 300 attempted to maximize ventricular expansion as measured by the impedance minimum, method 320A attempts to maximize the atrial contribution to ventricular filling as measured by the change in impedance between atrial activation and maximal ventricular volume before ventricular contraction. While method 300 could utilize a constant AV interval during the search for minimum impedance, method 320A actively varies the AV interval in the search for the optimal AV interval. In step 322, the AV interval can be initialized to an initial AV interval value. In some embodiments, the AV interval is initialized to an initial AV interval believed to be optimal based on previous determinations.

In step 324, the atrium can be sensed or paced, then the ventricle paced, using the current AV interval. In step 326A, the impedance can be measured at time points near A-event. In one method, the impedance is measured near the A-event, either shortly before or shortly after the A-event, preferably shortly after the A-event. The impedance can be measured again near the V-pace event, either shortly before, during, or after the V-pace. The impedance measurement taken near the V-pace should correspond to the maximum expansion and minimum impedance. The impedance will normally drop from the A-event to the V-pace.

In some embodiments, step 326A measures the impedance over N beats, where N can be one or greater. The impedance data thus obtained can be averaged to obtain an average impedance minimum and maximum for the same AV interval. In another method, taking impedance measurements for the same AV interval over N beats, the delta Z itself can be averaged over several beats having the same AV interval.

In step 328A, the delta Z, the difference between the maximum impedance and the minimum impedance measured, can be determined. In decision step 330, the determination can be made whether the AV interval causing the maximum delta Z has been found, and the search completed. As will be discussed further, different algorithms can be used to determine whether the searching for the optimal delta Z by varying the AV interval has been completed or requires further iteration. In step 330, if the maximum delta Z has not yet been found, then step 334 can be executed to search further for the maximum delta Z by changing the AV interval. The search algorithms used will be discussed below. In step 334, the AV interval can be changed to intelligently bracket the maximum delta Z and search for the maximum delta Z. The search and the changing of the AV interval can be based upon the recent history of previous values obtained for various AV intervals. If the maximum delta Z has not been found, after changing the AV interval at 334, step 324 can be executed using the new AV interval.

The above discussed steps can be repeated until step 330 determines that the maximum delta Z has been found, or the algorithm times out. When the maximum delta Z has been found at 330, step 332 can be executed to set the paced AV interval to the AV interval corresponding to the maximum delta Z. As previously discussed, the impedance measured in step 326A is preferably measured using a sub-threshold pulse, rather than a pacing pulse. In an alternate embodiment, the pacing pulse is used to measure at least one of the impedance values near the minimum and/or maximum.

Figure 5B:
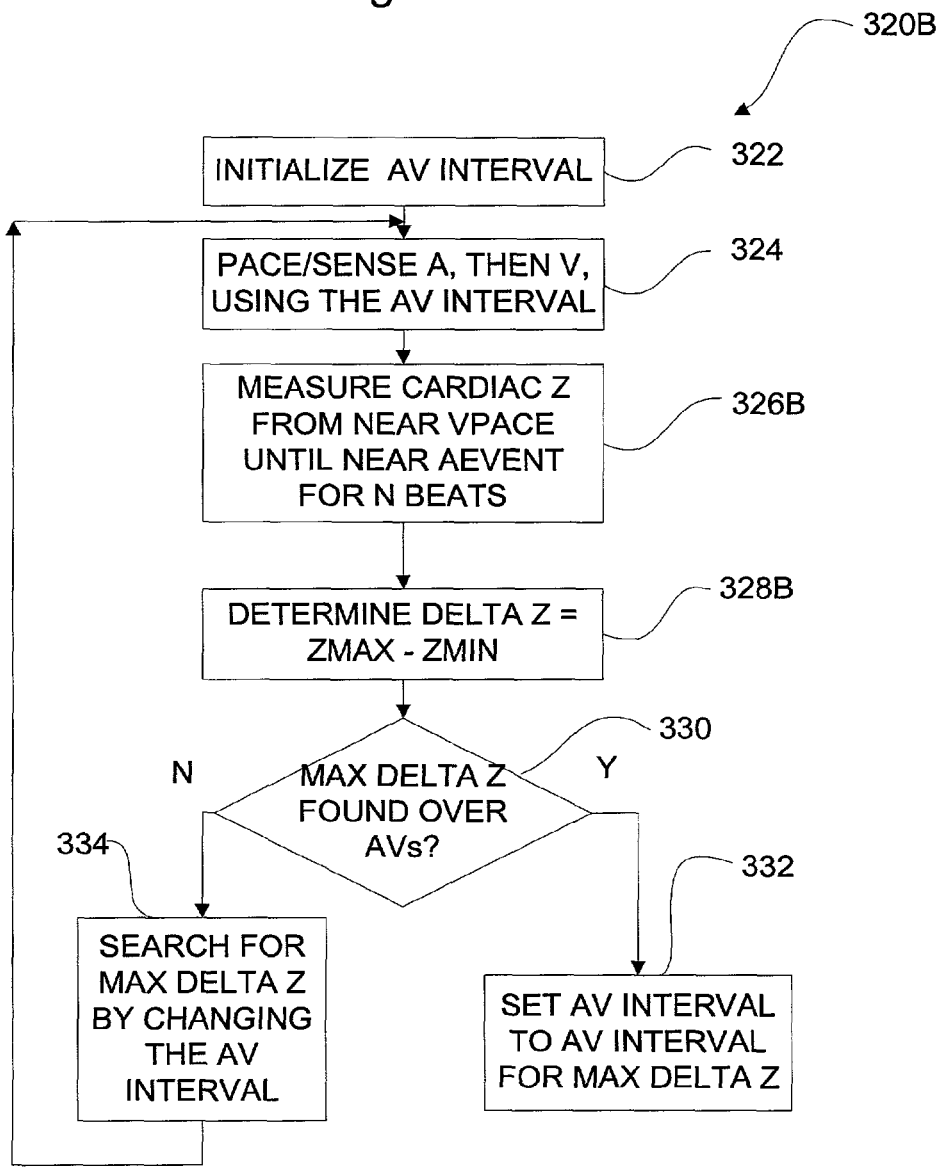
FIG. 5B is a flow chart of a method for obtaining an optimum AV interval by intelligently varying the AV interval to search for the AV interval causing a maximum impedance change measured between a cardiac cycle minimum and a cardiac cycle maximum impedance located between V-pace and the next A-event, corresponding to a maximum cardiac output.

FIG. 5B illustrates another embodiment 320B for optimizing the AV interval. While method 320A attempted to maximize the impedance drop, from A-event to V-pace, method 320B attempts to maximize the increase in impedance from a minimum, usually near V-pace, to a maximum, located between the V-pace and the next A-event. Identically numbered steps in method 320B and 320A, have already been discussed with respect to method 320A in FIG. 5A, and will be repeatedly discussed.

In step 326B, the impedance can be measured at time points from near V-pace until near A-event, in order to catch the peak or maximum impedance located between the two events. In one method, the impedance is measured near the V-pace, either shortly before, during, or shortly after the V-pace, until either the maximum impedance is detected or until the A-event is detected, with the maximum impedance having been captured.

In some embodiments, step 326B measures the impedance over N beats, where N can be one or greater. The impedance data thus obtained can be averaged to obtain an average impedance minimum and maximum for the same AV interval. In another method, taking impedance measurements for the same AV interval over N beats, the delta Z itself can be averaged over several beats having the same AV interval.

In step 328B, the delta Z, the difference between the maximum impedance and the minimum impedance measured, can be determined. As previously discussed, in some methods, the impedance near V-pace is used in place of a minimum measured impedance, as the impedance near V-pace is typically very low.

FIG. 6 includes a flow chart for embodiment 340 which varies the VV interval to find the maximum impedance. The maximum impedance corresponds to the maximum ventricular contraction and minimum ventricular volume. Method 340 optimizes the VV interval indicating the amount of time by which the right ventricle leads or lags the left ventricle. The VV interval may also be viewed as having a separate atrium to right ventricle delay and a separate atrium to left ventricle delay. The VV interval may also be referred to as the inter-ventricle time difference.

In step 341, the VV interval can be initialized in some methods to 0. In step 342, the AV interval can be initialized and maintained at a constant, preferably, optimal AV interval. In some methods, the optimal AV interval as determined by methods such as method 300, 320A, or 320B can be used to set the optimal AV interval.

In step 344, the atrium A-event occurrence can be paced or sensed, then the first ventricle paced, then the second ventricle paced, using the AV interval from step 342 and the VV interval. Whether the right ventricle is the first ventricle or the left ventricle is the first ventricle paced depends upon whether the right ventricle leads or lags the left ventricle, respectively. In a preferred embodiment, the AV interval refers to the time delay between the RA-event and the LV-pace. In other embodiments, the AV interval refers to the time delay between the RA-event and the first V-pace or to the time delay between the RA-event and the second V-pace, while in still other embodiments, the AV interval refers to the time delay between the RA-event and the average between the two V-paces.

In step 346, the impedance can be measured at multiple times. In one method, the impedance is measured at one or more times shortly after a V-pace and at one or more times either shortly before, during, or shortly after the next A-pace event, in order to catch the cardiac cycle maximum impedance, as previously described. As previously discussed, while the impedance can be measured using pacing signals, separate, sub threshold signals are used in a preferred embodiment. In another embodiment of the invention, the impedance is measured at multiple times after a V-pace until the next A-event to determine the maximum impedance. The impedance at or near a V-pace can be used in place of the minimum impedance, as previously discussed, in some methods. Measuring step 346 can be repeated for the same VV interval for a number of consecutive beats in order to obtain an average for the maximum impedance value found. An averaged waveform, averaged over several cardiac cycles, can also be used to determine the maximum impedance.

In step 348, the maximum impedance found for the VV interval can be determined. As previously discussed, the maximum impedance corresponds to the state of maximum ventricular contraction, indicating the ventricles have emptied. The maximum impedance found in step 348 is the maximum impedance found for the current VV interval.

In decision step 350, a determination is made as to whether the VV interval causing the maximum impedance has been found for the allowable range of VV intervals. The algorithms and search methods which can be used in combination with method 340 are discussed in more detail below. If step 350 determines that the VV interval having the maximum impedance has not been found, then step 354 can be executed to further search for the maximum impedance by changing the VV interval. Step 354 can change the VV interval, preferably using the recent history of impedances found for other VV intervals. Step 354 can intelligently search for the optimal VV interval by bracketing the maximum impedance based on the recent history of impedance values found. Using the new VV interval found in step 354, step 342 can be executed.

When decision step 350 determines that the VV interval having the maximum impedance has been found, then step 352 can be executed to set the pacing VV interval to the VV interval corresponding to the maximum impedance found. In some methods, after step 352, AV interval optimization methods such as method 300 or 320 can be executed to re-optimize the AV interval using the VV interval recently optimized. The AV interval may thus be optimized while maintaining a time difference between the V-pace for the right ventricle and the V-pace for the left ventricle.

Figure 7:
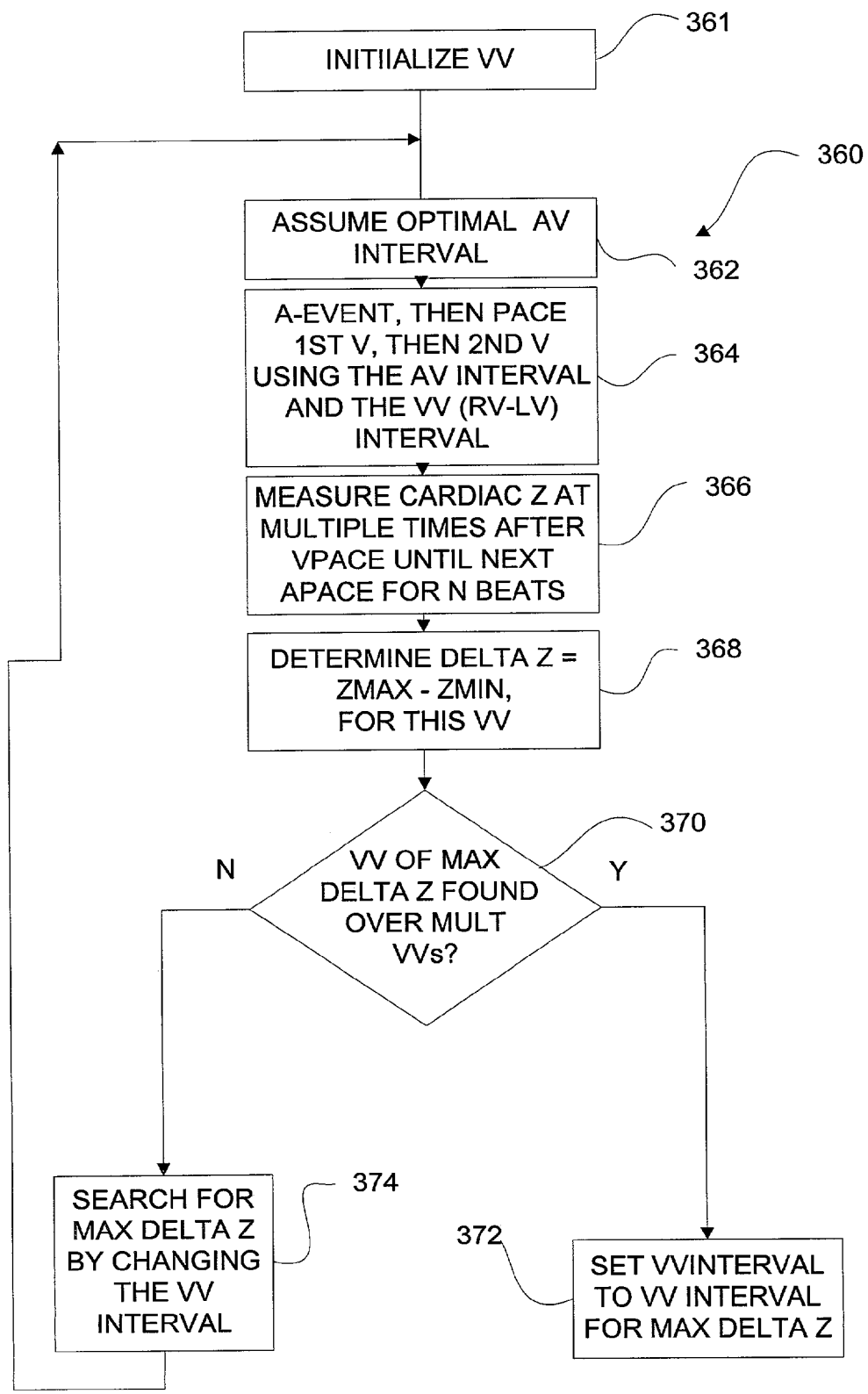
FIG. 7 is a flowchart of a method for optimizing the inter-ventricular delay by intelligently varying the inter-ventricular delay and searching for the delay having a maximum impedance change corresponding to a maximum cardiac output.

In FIG. 7, method 360 is used to optimize the VV interval. As used herein, the VV interval refers to the delay between the pacing of the right ventricle and the left ventricle. The VV interval may also be referred to as the inter-ventricle time difference or timing difference. The VV interval may thus be positive or negative, depending on whether the right ventricle leads or lags the left ventricle. As previously discussed, method 360 may be executed in the various clinical and ambulatory settings having various preconditions, which will be discussed later.

In step 361, the VV interval can be initialized to a time, which is 0 in some methods. In step 362, the AV interval can be set to a constant, preferably an optimal AV interval as determined by methods such as method 300 of FIG. 4, method 320A of FIG. 5A or method 320B of FIG. 5B.

In step 364, the atrium can be sensed or paced, followed by the first ventricle being paced, followed by the second ventricle being paced. Step 364 can thus use the AV interval of step 362 and an initial VV interval. In some methods, the VV interval is initially set to zero. In some methods, the AV interval as used in method 360 refers to the timing between the A-event and the first ventricle V-pace, while in other methods the AV interval refers to the timing between the A-event and the second V-pace, while in still other methods, the AV interval refers to the time delay between the A-event and the average time of the ventricular paces. Depending on the VV interval, either the right or the left ventricle may be the first or second ventricle, respectively. As previously mentioned, the VV interval can be a positive or a negative number in some implementations of the method.

In step 366, the impedance can be measured at multiple times. In one method, the impedance is measured at one or more times shortly after a V-pace and at one or more times either shortly before, during, or shortly after the next A-event, in order to catch the cardiac cycle maximum impedance, as previously described. As previously discussed, while the impedance can be measured using pacing signals, separate, sub threshold signals are used in a preferred embodiment. In another embodiment of the invention, the impedance is measured at multiple times after a V-pace until the next A-event to determine the maximum impedance. The impedance at or near V-pace can be used in place of the minimum impedance, as previously discussed, in some methods. Measuring step 366 can be repeated for the same VV interval for a number of consecutive beats in order to obtain an average for the maximum impedance value found. An averaged waveform, averaged over several cardiac cycles, can also be used to determine the maximum impedance.

In step 368, the change in impedance for this VV, delta Z, can be determined by taking the difference between the maximum impedance and the minimum impedance. In step 370, the determination can be made as to whether the maximum change in impedance over a range of VV intervals has been found, and the search complete. The exact nature of the many possible algorithms used to make this determination are discussed below. If the VV causing the maximum delta Z has not been found, then the search can be continued by changing the VV interval, and proceeding to step 362. The VV interval is preferably changed based on the recent history of impedances obtained for other VV intervals. This process can continue until decision step 370 makes the determination that the maximum delta Z has been found, or the algorithm times out. When the maximum delta Z has been found, step 372 can be executed. In step 372, the VV interval can be set to the VV interval corresponding to the maximum delta Z. In some embodiments, the AV interval can be re-optimized using methods such as method 300 or 320, previously discussed.

The impedance signal used to measure the change in degree of contraction and expansion of the heart is typically a composite signal. The composite signal has a low frequency, large amplitude impedance change contribution from the breathing of the patient. The impedance measurement is greatly affected by the distance between the measuring electrodes. The distance between the measuring electrodes is greatly affected by the breathing. The breathing contribution has a nominally sinusoidal wave form having a period of between about 5 and 10 breaths per minute. In contrast, the cardiac contribution to the impedance change has a smaller amplitude and a nominal period of about 60 beats per minute. The smaller amplitude, higher frequency cardiac impedance wave form is thus superimposed on the larger amplitude, slower frequency breathing impedance wave form. The contribution of breathing can be compensated for using varying methods.

Figure 8:
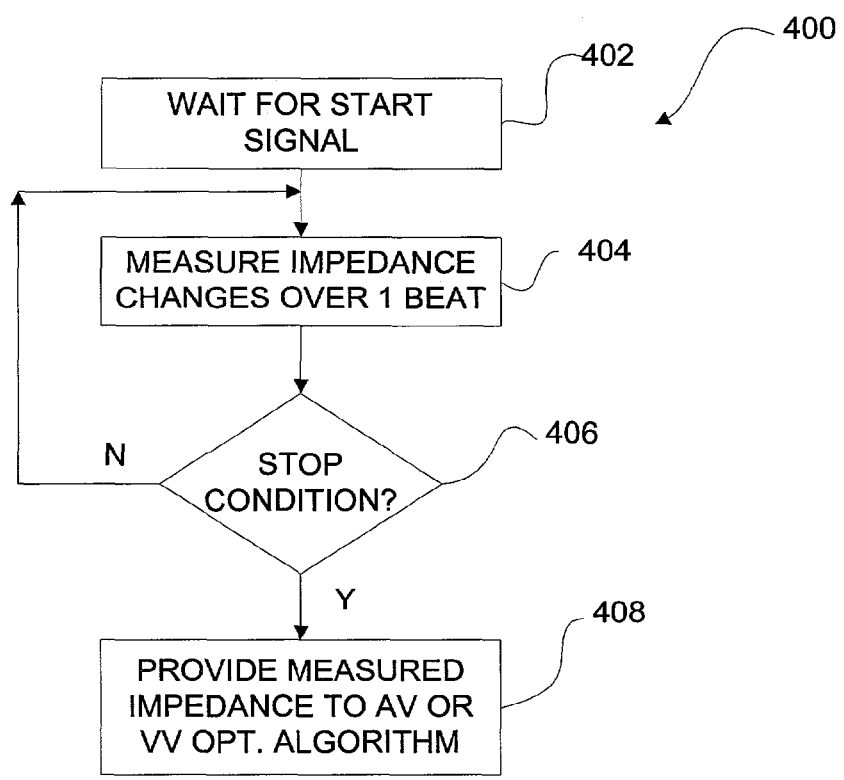
FIG. 8 is a flow chart of a method for obtaining cardiac impedance data in clinical setting using breath holding as directed by a physician.

FIG. 8 illustrates an embodiment 400 for providing impedance data, to the interval optimization methods previously discussed. Method 400 is one example of a method for providing impedance data, which is preferably used in a clinical setting. In step 402, method 400 waits for a start signal. The patient is preferably supine, not moving, and has a regular breathing pattern. A treating physician can wait for the patient to be appropriately disposed then send a start signal from a programming unit, through a telemetry link, to the implanted pacing device. In step 402, the pacing device receives the start signal from the programmer, and proceeds to step 404.

In step 404, the implanted pacing device can automatically adjust pacing parameters as needed to carry out the interval optimization methods previously discussed to measure the impedance changes over one or more heartbeats. In the example illustrated, the impedance is measured over a single beat. With the impedance measured over one beat, decision step 406 is executed, checking for the existence of a stop condition. If the stop condition is not found, step 404 can be executed, to gather data from another heartbeat or beats. In a preferred method, the start signal is not sent until the patient is both supine, not moving, and further, has temporarily held their breath. In one example method, the treating physician instructs the patient to hold their breath, and upon observation of the breath holding, sends the start signal. In some embodiments, the stop condition at step 406 consists simply of a timer or heartbeat counter which gathers data over a certain time interval of heartbeats or number of heartbeats. In another embodiment, a large degree of patient movement as determined by an accelerometer and/or a large change in impedance indicating breathing may be used to initiate the stop condition at step 406. After one or more beats has been measured for impedance at step 404, and the data gathering stopped, step 408 can be executed. In step 408, the measured impedance can be provided to one of the AV or VV optimization methods previously described.

Figure 9:
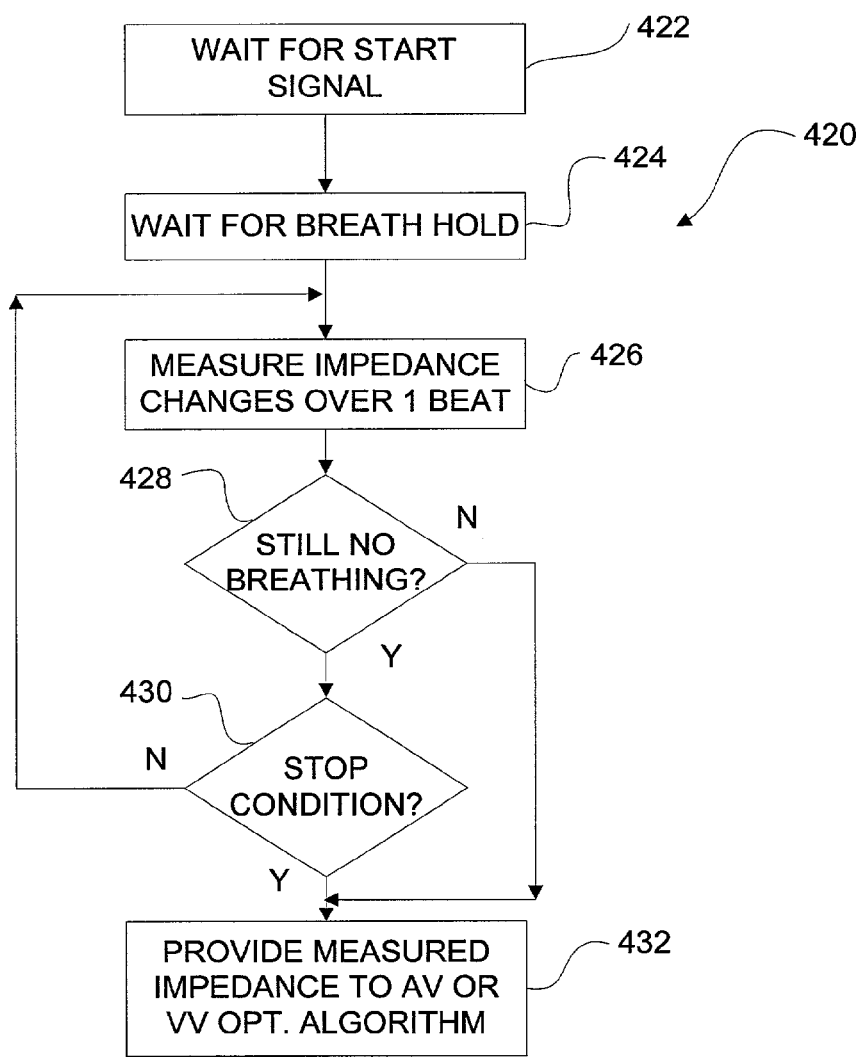
FIG. 9 is a flowchart of a method for obtaining impedance data in a clinical setting during a sensed breath hold.

FIG. 9 illustrates another embodiment 420 for providing impedance data to the optimization methods previously discussed. Method 420 is similar to method 400 previously discussed, but waits for a detected breath hold as an integral part of the algorithm rather than depending upon the physician to observe the breathing cessation. In step 422, the method waits for the start signal, for example, from a programmer unit communicating to the implanted device via a telemetry link.

In step 424, the logic waits for a breath hold. Breath holding may be detected by any of a number of methods. In one method, the impedance data is tracked and filtered to detect the long period impedance changes of large amplitude, indicative of breathing. In another method, an impedance measurement to detect breathing is used that is different from the impedance measurement used to optimize the AV and VV intervals. In one example, a transthoracic impedance between the implanted pacing device housing and a cardiac lead are used to detect breathing. In still another embodiment, an accelerometer, for example, based either in the housing or on a lead, is used to detect breathing.

When the breath hold is detected in step 424, step 426 can be used to measure the impedance changes, as the impedance changes due to the pumping of the heart are more easily measured without the larger breathing contribution. In decision step 428, if breathing is still ceased, and no stop condition is detected as decision step 430, impedance can be measured at step 426 for another beat or another time period. As previously discussed, a stop condition such as at step 430 can be the detection of bodily movement as detected through an accelerometer, the expiration of a timeout period, the successful sampling of a maximum number of beats, or an abnormally high change in impedance. Step 426 can thus be executed for a number of beats. When the required number of beats has been measured for impedance and/or breathing has resumed, the measured impedance can be fed to one or more of the optimization methods previously discussed. The logic in embodiment 420 may be executed several times in succession, feeding new impedance data to one of the AV or VV optimization algorithms previously discussed. Specifically, the breathing contribution to impedance is compensated for by a temporary holding of breath, providing a constant contribution to impedance by the breath hold.

Figure 10:
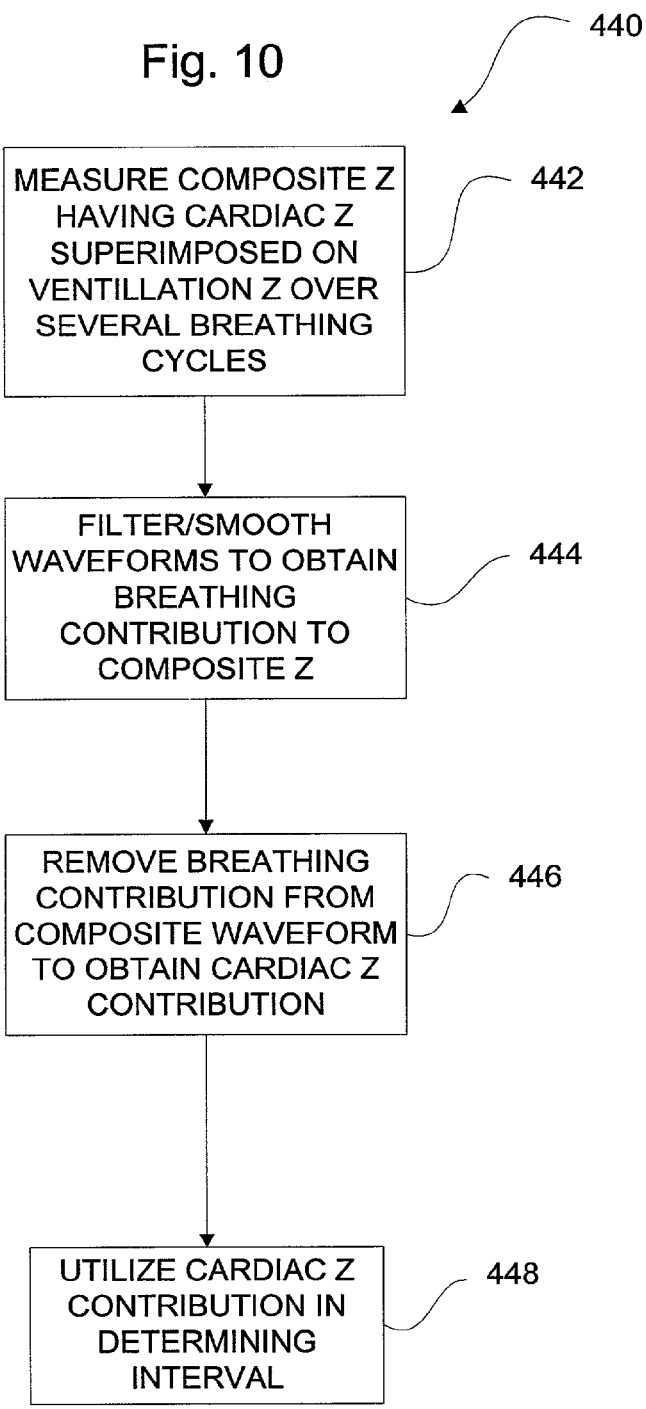
FIG. 10 is a flowchart of a method for obtaining impedance data by removing the slower frequency breathing contribution from the composite impedance signal.

FIG. 10 illustrates yet another embodiment 440 for providing impedance data to the AV and VV interval optimization methods previously discussed. In step 442, the composite impedance wave form is measured, preferably over several breathing cycles. The composite impedance thus has the higher frequency cardiac impedance change wave form superimposed on the lower frequency, larger amplitude breathing impedance change wave form.

In step 444, the breathing contribution to the composite impedance wave form can be obtained by filtering or smoothing the composite wave form to obtain the breathing impedance wave form alone. Other suitable methods, well known to those in the signal processing arts, can be used to separate the breathing impedance wave form from the cardiac impedance wave form.

In step 446, the breathing contribution can be removed from the composite wave form to obtain the cardiac impedance wave form contribution. Other methods well known to those in the signal processing arts can be used to obtain the higher frequency cardiac impedance wave form from the composite wave form. In step 448, the cardiac impedance contribution can be provided to one or more of the interval optimization methods previously discussed.

Figure 11:
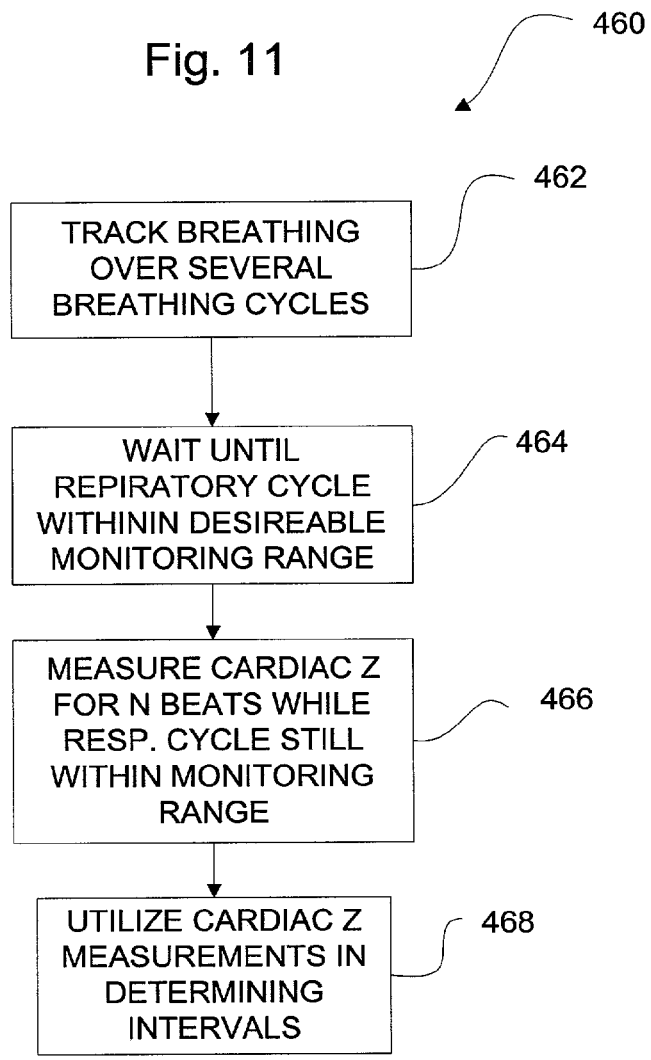
FIG. 11 is a flowchart of a method for obtaining impedance data during a voluntary sensed breath hold.

FIG. 11 illustrates a flow chart of embodiment 460 which can be used to select periods of breath holding in order to obtain cardiac impedance change data that is less effected by breathing. In step 462, the breathing can be tracked over several breathing cycles. This tracking can be done using various devices and methods, not necessarily using the same methods and/or sensors used to measure the cardiac impedance. In some examples, implanted cardiac device housing based accelerometers or lead based accelerometers can be used to track breathing apart from the impedance measurement. In a clinical setting, a belt disposed about the patient's chest can be used to sense breathing as can a pressure or heat sensitive device disposed near the mouth and/or nose. Other devices for tracking breathing, commonly used in demand or physiologically based pacing, can be used to track breathing as well.

In step 464, a breath hold can be awaited. When a breath hold has been detected at step 464, the impedance can be measured for a number of beats or a number of time intervals while there is still no breathing detected, at step 466. After the required number of beats or time intervals has elapsed and/or breathing has been detected, the cardiac impedance change data can be collected at step 468 and used in one of the AV or VV interval optimization methods previously discussed. Method 460 thus illustrates a method which can be used to optimize AV or VV intervals by the patient holding their breath for a required period to initiate the optimization procedure.

Figure 12:
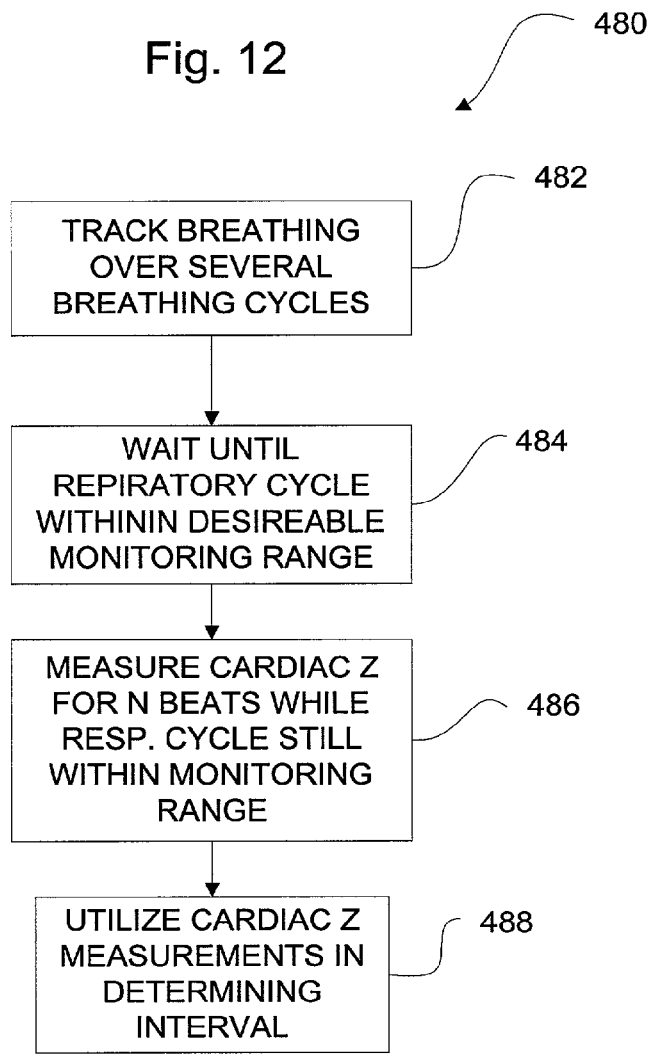
FIG. 12 is a flowchart of a method for obtaining impedance data by gating, selecting impedance data during a sensed region with minimal respiration changes.

FIG. 12 illustrates another embodiment 480 which can be used to provide impedance data to the interval optimization methods previously discussed. Method 480 illustrates a method using selection or "gating" during appropriate parts of the breathing cycle to obtain good impedance data. In method 480, impedance data are obtained near the peak of the inspiration and/or nadir of the expiration phase regions, which are less effected by respiratory changes to the impedance signal. In step 482, breathing can be tracked over several breathing cycles, using devices and methods previously discussed, including accelerometers and transthoracic impedance measurements. In some methods, a monitoring range or window is used. This range is defined as a time window around the peak or nadir or other time point on the respiration cycle in which the respiration changes are small. One method uses the observation that the first derivative of the respiration signal can be taken to see when respiration changes are at a minimum. In step 484, the method waits for breathing expiration. In some methods, breathing inspiration can also be used. As the monitoring range is detected, step 486 can be executed to measure the impedance changes for N beats or N time periods while still in the monitoring range. Numerous submethods can be used to detect the nadir of the respiration cycle. The impedance measurement can be taken from a monitoring window or range in which the respiration component is relatively small.

Figure 13:
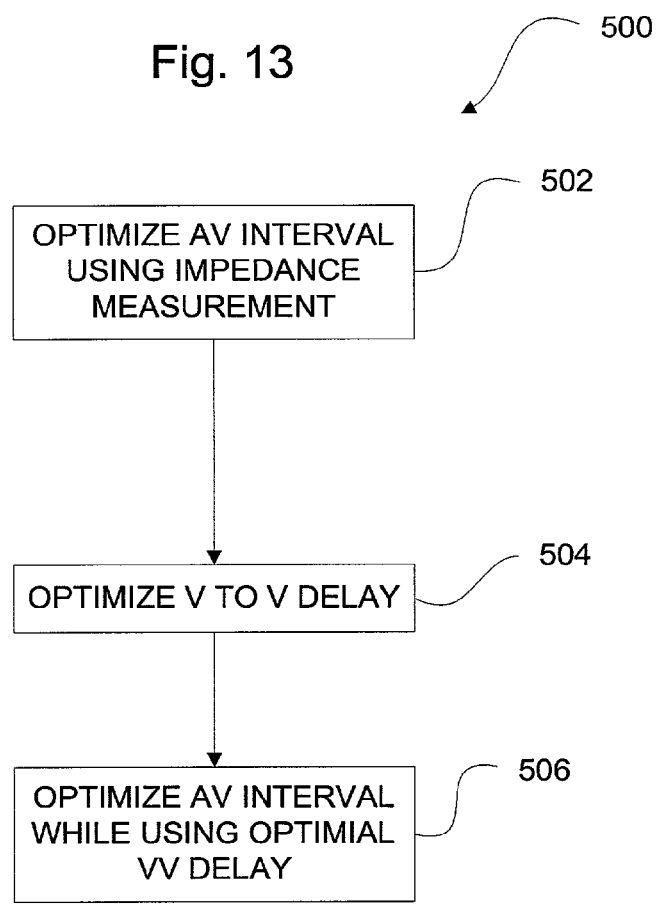
FIG. 13 is a flowchart of a method for optimizing AV interval, then VV interval, then re-optimizing the AV interval using the VV interval.

FIG. 13 illustrates an embodiment 500 for optimizing heart pumping operations generally. In step 502, the AV interval is selected to optimize heart pumping action. After initially optimizing the AV interval, step 504 is executed to optimize the VV interval. With the VV interval selected to optimize cardiac output, step 506 is executed to once again optimize the AV interval while using the VV interval provided by step 504. In one example, methods such as method 300, 320A, or 320B are used to optimize the AV interval using a VV interval of zero in step 502. In step 504, methods such as method 340 or 360 are used to select a VV interval for optimal cardiac output. With the VV interval selected, the right ventricle will either lead or lag the left ventricle, for a non-zero VV interval.

In step 506, embodiments such as embodiment 300, 320A or 320B can be once again executed, this time incorporating an optimal VV interval. Thus, the AV interval utilized in method 300 or 320 will include the right ventricle and the left ventricle being paced at different times. In one example, the AV interval thus optimized will refer to the A to first interval delay while in other methods, the AV interval will refer to the atrial to second interval delay, while in still other embodiments, the atrial to ventricle period will refer to the atrial to average ventricular pace time. In this way, using method 500, the AV synchrony can be still further optimized.

Figure 14:
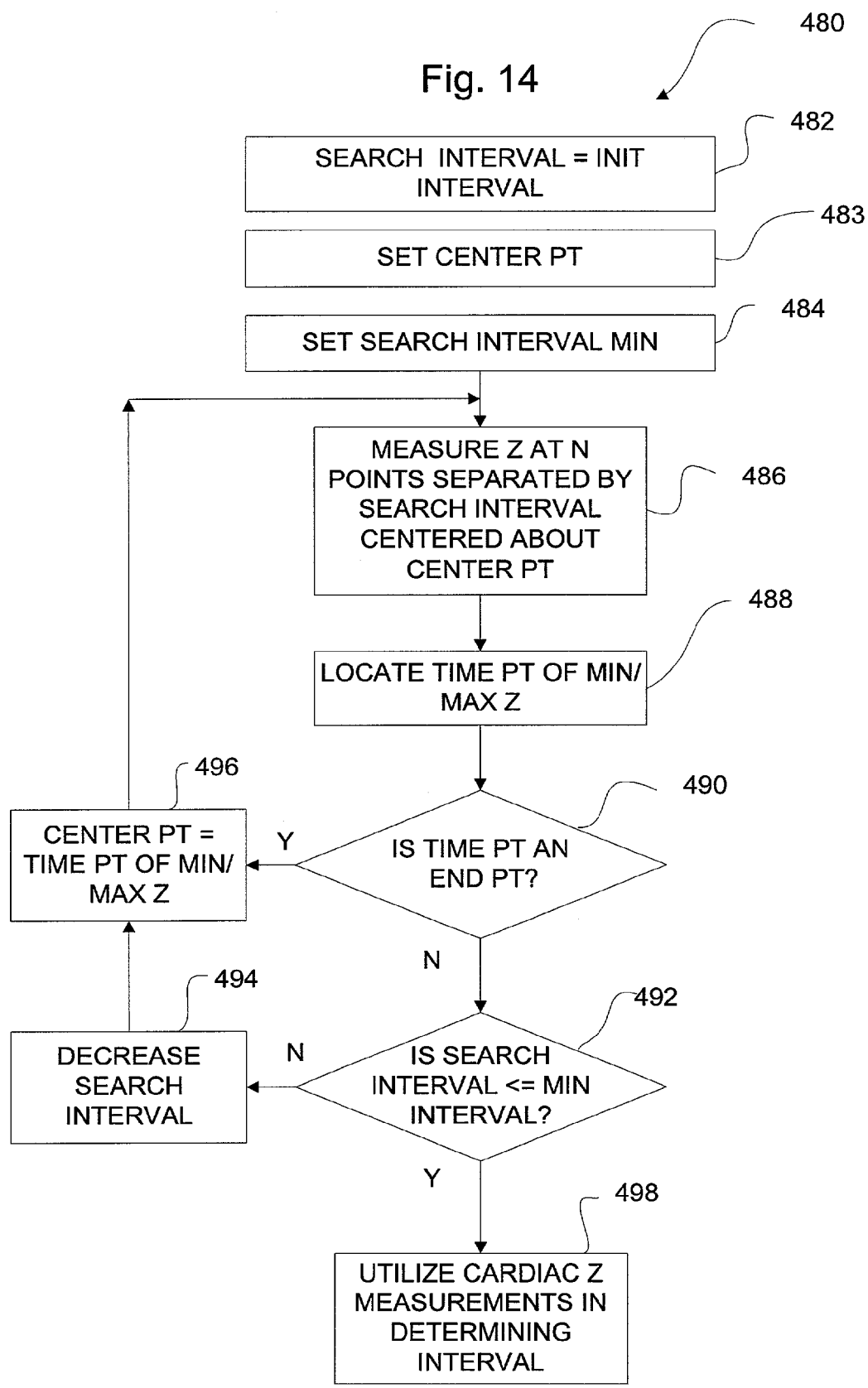
FIG. 14 is a flow chart of a general method for searching for times having optimal impedance values or changes.

FIG. 14 illustrates a search embodiment 480 which can be used in various embodiments of the present invention. In particular, method 480 can be used in steps such as step 330 and 334 of method 320A and 320B, steps 350 and 354 of method 340, and steps 370 and 374 of method 360.

In one embodiment, method 480 operates as a "binary search." In methods such as method 300, a wide variety of search algorithms can be used as a number of impedance values may be provided over the cardiac cycle. In methods 320A, 320B, 340 and 360, however, the ventricle or ventricles can be paced only once per cardiac cycle, thus benefiting from a more intelligent search.

In step 482, a search interval can be initialized to an initial search interval. The search interval may be viewed as the interval between the time points which will be spaced within the longer time window of all the maximal possible AV or VV interval. In one example, the initial search interval may be about 40 or 20 milliseconds. In step 483, the center point is set as bisecting the search interval. In step 484, the search interval minimum can be set to indicate the required lower limit on the search interval in order to satisfy the search completion requirement. In other words, when the search has found a minimum or maximum, and the search interval is sufficiently small, then the search will be considered complete, and the overall minimum or maximum will be considered as found. In contrast, if a minimum or maximum has been found but the search interval is large, for example, 50 milliseconds, the search will likely continue in many embodiments to find a more accurate representation of the timing leading to the minimum or maximum. In one embodiment, the search interval minimum is set to about 5 milliseconds.

In step 486, impedance is measured and/or pacing is performed at end points separated by the search interval centered about a center point. In the example of a binary search, pacing may occur at three different time points separated by the search interval and separated about the center time point. In the example of a binary search having a center time point of 100 milliseconds and a search interval of 40 milliseconds, the three time points will be 60 milliseconds, 100 milliseconds, and 140 milliseconds. The allowable range of time points may of course be clamped at safety limits at either end. In the case of a binary search, having three time points, there will be formed two segments, one each extending from an end point toward the center point. In the operation of the algorithm, it is not known a priori where the maximum or minimum will be. Where the step 486 is pacing at end points, step 486 will be executed over several heartbeats. In embodiments where averaging is used, even more heartbeats will be used as the same pacing time point will be executed for multiple heartbeats.

In step 488, the time point having the minimum or maximum, depending on the embodiment, will be noted. The time point is thus the minimum or maximum of the end points measured and/or paced in step 486.

In decision step 490, it is determined whether the time point of minimum or maximum impedance is an end time point. If the minimum or maximum occurs at an end point, the true minimum or maximum may lay beyond the end point, and further searching is required. In this case, execution proceeds to step 496, where the center point of the next search is centered at or toward the time point of minimum or maximum found in step 488. In some methods, the new center is slewed toward the time point of minimum or maximum impedance, while in other embodiments, the center point is set exactly at the time point of minimum or maximum impedance.

With the next search properly centered, the search interval can be decreased or left the same. In one embodiment, the search interval is unchanged when the search window is effectively moving sideways, rather than converging on the minimum or maximum. In the binary search example, having a search centered at 100 and sampling or pacing at 140 and 60 milliseconds, if the minimum or maximum was located at 140, the next search could be centered about 140 and extending up to 180 and down to 100. In a preferred embodiment, time points representing previously visited points are recalled from memory rather than being resampled or repaced. In another method, the end points of step 486 are resampled and/or repaced at each execution of step 486.

Embodiment 480 thus executes from step 490 through 496 until a minimum or maximum is found that is not an end point. When a minimum or maximum is found that is not an end point, then decision step 492 can be executed. In some embodiments, a specific degree of centrality is required to execute 492. For example, in some embodiments, the located maximum or minimum time must be the absolute center of the search interval or at least be the central point.

In decision step 492, a determination is made where the search interval is sufficiently small to end the search. In particular, it can be checked whether the search interval is less than or equal to the minimum search interval. In one example, in order to successfully complete the search, the search interval must be 5 milliseconds or less. If the search interval is not sufficiently small, execution can proceed to step 494 where the search interval is decreased. In one example, the search interval is halved in step 494. Proceeding to step 496, the center point can be set to the, or toward the, time point corresponding to the minimum or maximum impedance found in step 488. In some embodiments, step 496 thus centers the search for the same number of points and the same center search point as the previous execution of step 486, but with a small search interval. As previously discussed, in some embodiments, the measurement and/or pacing at a time point is not revisited if the time point has been measured and/or paced recently. In these embodiments, the impedance or impedance change value can be retrieved from recent memory. In other embodiments, all end points are revisited in step 486.

When the search interval lower limit has been satisfied in step 492, step 498 can be executed. The desired minimum or maximum impedance or impedance change can be provided in step 498 and utilized by the methods to optimize the AV or VV intervals previously discussed.

Embodiment 480 is a general algorithm which can be used to rapidly bracket or converge on the minimum impedance, maximum impedance, or maximum impedance change. A variation on method 480 may be briefly described. In step 496, the center point for the next search may also be established by interpolating between the best impedance value found and the next best impedance value found. In one example, searching for the impedance maximum, the time point of the maximum impedance and the time point of the next highest impedance may be interpolated between to obtain the new center point for the search. Similarly, in a search for an impedance change maximum, the pace time having the maximum impedance change and the pace time having the second maximum impedance change may be used and the new center point for the next V-pace may be interpolated between the two points.

In another embodiment of the invention, a binary search embodiment, the initial interval is divided by one point into two search segments. The best point is noted, as is the next best point. If the best point is an end point, the search is shifted over, making the previous end point the center point, and the search evaluated again. If the best point is a center point, but the search interval lower limit is not satisfied, then the next search subdivides the segment between the best point and the next best point and evaluates the impedance there. The search interval is thus half the search interval as the previous search interval. If the point evaluated midway between the previous best point and next best point is again the local maximum, and the search interval is sufficiently small, then the search is complete, and the optimal interval has been found. If the most recently evaluated point is not the best point, then the segment between the best point and the worst point is subdivided and the best point again search for among the points.

The present invention can use a binary search algorithm to find the minimum impedance, the maximum impedance, or the maximum impedance change over a window of time values, from low to high. As the method can be used with goal of finding the time point having the best impedance values generally, whether minimum, maximum, or maximum change, the method may be explained generally in terms of finding the best impedance. Several binary search variations can be used. In general, the binary search starts with a set of three time points, low, middle, and high, having low, middle, and high time values, respectively, separated by a search time interval. The three time points divide the time range into two subintervals, from low time to middle time, and from middle time to high time. The binary search, explained generally, starts with initial high and low time points, and a lower limit search interval time or goal.

One embodiment evaluates impedance at the three time points, low, middle, and high, separated by the time search interval. If the "best" impedance is found at the middle point and the search interval is less than or equal to the lower limit search interval goal, then the middle time point can be returned as the time point having the best impedance. If the best impedance is found at the middle point and the search interval is greater than the lower limit search interval, then the search interval can be halved, and the search repeated using as the new middle point the point midway between the old middle point and the second best time point.

In the case where the best impedance is found at one of the end points, then the search interval is unchanged, and the search is repeated centered on the new end point, effectively sliding the search window over in time. In this way, the method can use the optimal time points from previous optimizations as the initial first estimate at the best time point for a later optimization, yet remain sufficiently robust to slide the search window over when the current optimal time is located outside of the initial search window.

Figure 15:
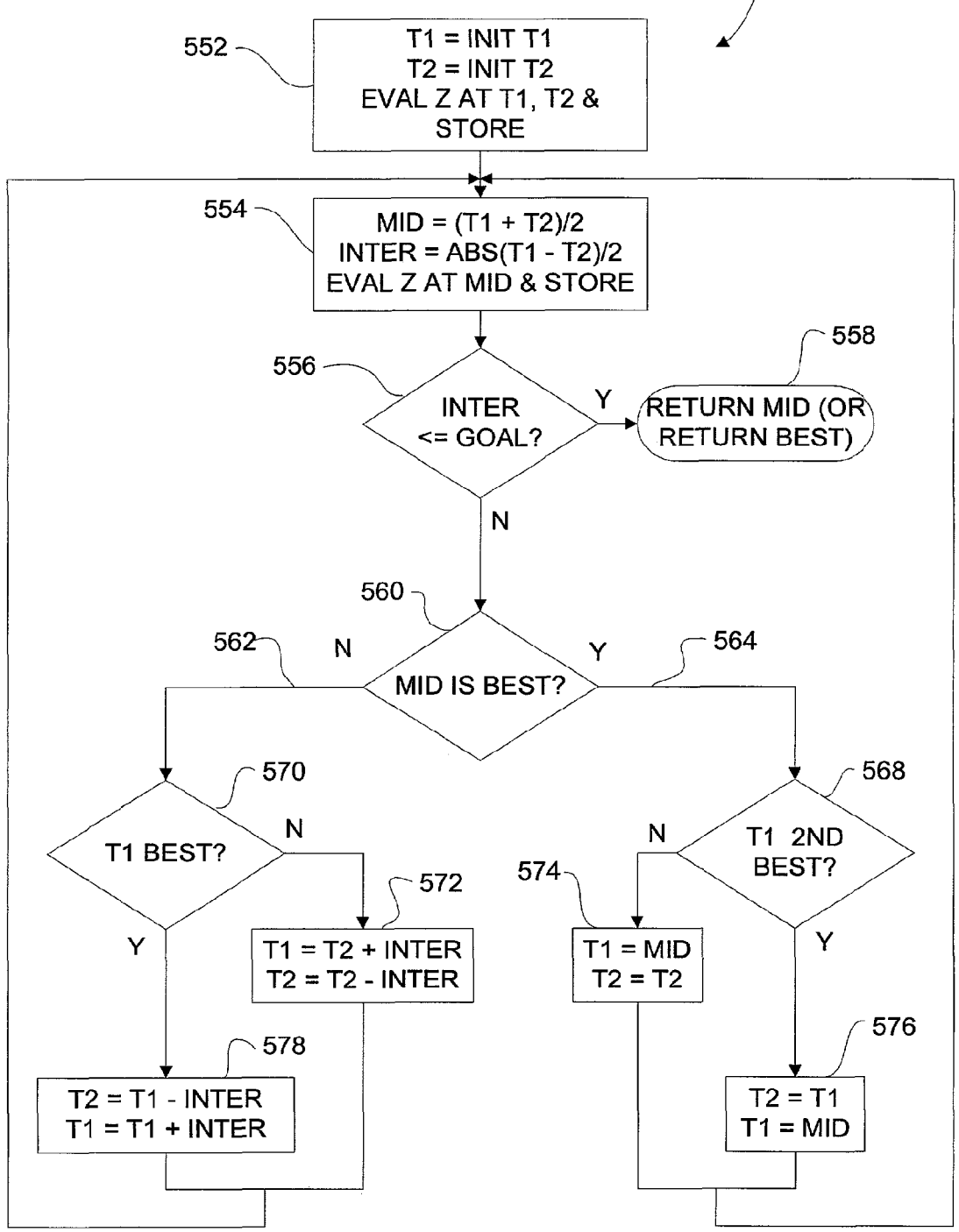
FIG. 15 is a flow chart of a binary search method for searching for times having optimal impedance values or changes.

FIG. 15 illustrates a binary search embodiment 550, starting at an initialization step 552, initializing two time points T1 and T2, which can be the low and high time points of the search window, in any order. The impedance (Z) can be evaluated for both T1 and T2. In one embodiment, the impedance for a time point is referenced by a function or array, where the actual sensor value is retrieved only if there is no recent sensor value for that time point.

In step 554, a middle time point, MID is set to bisect T1 and T2, being set equal to (T1+T2)/2. The current search interval, INTER, is set equal to half the distance between T1 and T2, and is the length of each of the two segments created by MID to T1 and MID to T2. The impedance can be evaluated at MID.

In decision step 556, if the search interval INTER is sufficiently low, then the search goal is met, the search is done, and step 558 is executed. In step 558, the best impedance value can be returned. In some methods, the middle time point MID is returned as having the time of best impedance. In other methods, the best of the time points T1, MID, and T2 is determined, with the best of the three returned as the time point of best impedance.

If the search is not complete, then step 560 is executed, to determine if the middle time point MID had the best impedance. If the best impedance was at MID, then step 564 is executed, to determine which of T1 and T2 was second best. If T1 was second best, then T2 is set to T1, and T1 is set to MID. If T2 is second best, then T1 is set to MID, and T2 remains unchanged. Step 554 can be executed once more, now using a search interval half the size, and bisecting the segment between MID and the second best point.

If decision step 560 determines that MID is not the best, then the best impedance is at an end point, and decision step 570 executes to determine if T1 is best. If T1 has the best impedance, then at step 578, T2 is set to T1 minus the current search interval INTER, and T1 is set to T1 plus the current search interval INTER. If T2 is best, then at step 572, T1 is set to T2 plus the search interval and T2 is set equal to T2 less the search interval. The new time points are set to bracket the end point that was the best point, with the search interval unchanged, and the search window slid over, to search again. It should be noted that in some binary search methods, execution does not branch on whether the best point is an end point, rather than the middle, with one of the segments being bisected regardless and the search continued. In this method, execution path 564 may be viewed as always being taken, and path 562 is effectively never taken.

The present invention explicitly includes within its scope implantable cardiac devices executing programs or logic implementing methods according to the present invention. The present invention's scope also includes computer programs or logic capable of being executed, directly or indirectly, on implantable cardiac devices. Computer readable media having instructions for implementing or executing methods according to the present invention are also within the scope of the present invention. Embodiments for producing impedance measurements compensated for breathing impedance or breathing impedance changes are explicitly within the scope of the invention as separate and independent methods, apart from their use in setting AV and VV intervals. Respiratory impedance compensating methods, devices implementing those methods, computer programs implementing those methods, and computer readable media containing programs implementing those methods are also within the scope of the invention.

The detailed description of the preferred embodiments provided herein yield a reliable and specific device and methods for automatic determination of optimal AV and VV intervals. Numerous variations of the described embodiments are possible for practicing the invention. Therefore, the embodiments described herein should be considered exemplary, rather than limiting, with regard to the following claims.

What is claimed is:

1. A method for setting an optimal right ventricle to left ventricle (VV) pacing interval for use in a pacing device, the method comprising:

searching for a VV interval causing the largest cardiac cycle maximum impedance, wherein the VV interval searching includes measuring the impedance in the cardiac cycle, determining the cardiac cycle maximum impedance, and varying the paced VV interval responsive to the cardiac cycle maximum impedance to converge on the largest cardiac cycle maximum impedance; and setting the VV interval pacing interval in the pacing device to the VV interval causing the largest cardiac cycle maximum impedance.

2. A method as in claim 1, wherein the searching includes varying the paced W interval to converge on the largest cardiac cycle maximum impedance in decreasing time intervals.

3. A method as in claim 1, wherein the searching includes binary searching to converge on the largest cardiac cycle maximum impedance.

4. A method as in claim 1, wherein the measuring impedance includes measuring the impedance at a plurality of time points beginning near a V-pace event until a next A-pace, and the determining maximum cycle impedance includes taking the largest measured impedance.

5. A method as in claim 1, wherein the measuring impedance includes measuring the impedance at a plurality of time points between a V-pace event and a next A-event to find the cardiac cycle maximum impedance.

6. A method as in claim 1, wherein the measuring impedance includes measuring the impedance at a plurality of time points after a V-pace event to find the cardiac cycle maximum impedance.

7. A method as in claim 1, wherein the measuring impedance includes measuring the impedance at a plurality of time points from a time window extending between about 30 milliseconds before and 100 milliseconds after a V-pace event, until near a next A-event, and the determining cardiac cycle maximum impedance includes taking the largest measured impedance.

8. A method as in claim 1, wherein the measuring impedance includes measuring the impedance at a plurality of time points beginning within a time window extending between about 10 milliseconds before and 30 milliseconds after a V-pace event, until a next A-event, and the determining maximum cycle impedance includes taking the largest measured impedance.

9. A method for setting an optimal right ventricle to left ventricle (W) pacing interval for use in a pacing device, the method comprising:

searching for a VV interval causing the largest cardiac cycle impedance change, wherein the VV interval searching includes measuring impedance in the cardiac cycle, calculating a cardiac cycle impedance change, and varying the paced W interval responsive to the cardiac cycle impedance change to converge on the largest cardiac cycle impedance change; and setting the VV interval pacing interval in the pacing device to about the VV interval causing the largest cardiac cycle impedance change.

10. A method as in claim 9, wherein the searching includes varying the paced W interval to converge on the largest cardiac cycle impedance change in decreasing time intervals.

11. A method as in claim 9, wherein the searching includes binary searching to converge on the largest cardiac cycle impedance change.

12. A method as in claim 9, wherein the measuring impedance includes measuring the impedance at a plurality of time points after a V-pace event until a next A-event, and the calculating cardiac cycle impedance change includes taking the difference of the largest and smallest measured impedance.

13. A method as in claim 9, wherein the measuring impedance includes measuring the impedance near a V-pace event and near the cardiac cycle maximum impedance, and the calculating cardiac cycle impedance change includes taking the difference of the largest measured impedance and the impedance measured near the V-pace event.

14. A method as in claim 9, wherein the pacing device is implanted in a patient and the patient has a breathing cycle including an inhaled maximum impedance time region and an exhaled minimum impedance time region, the method further comprising tracking the breathing cycle of the patient to produce breathing cycle data indicating a position within the breathing cycle, wherein at least part of the measuring impedance occurs during the exhaled minimum impedance time region to produce a measured impedance having minimal respiratory impedance change.

15. A method as in claim 14, wherein the tracking includes sensing movement using an accelerometer positioned on the implanted cardiac device housing.

16. A method as in claim 14, wherein the tracking includes sensing acceleration using an accelerometer positioned on a lead coupled to the cardiac device.

17. A method as in claim 14, wherein the tracking includes sensing impedance changes between electrodes having a substantial breathing impedance component.

18. A method as in claim 12, wherein the tracking sensing impedance changes measures impedance across a current path different than the current path used to measure the measuring impedance step, such that the tracking sensing impedance changes has a larger breathing impedance change contribution than the measuring impedance.

19. A method as in claim 9, wherein the pacing device is implanted in a patient and the patient has a breathing cycle including an inhaled maximum impedance time region and an exhaled minimum impedance time region, further comprising tracking the breathing cycle of the patient to produce breathing cycle positional data indicating the position within the breathing cycle, wherein at least part of the measuring cardiac impedance occurs during period of substantially unchanging breathing impedance contribution to produce an impedance measurement data set less affected by breathing.

20. A method as in claim 9, wherein the pacing device is implanted in a patient and the implanted cardiac device includes a telemetry component for receiving signals from a programming unit disposed external to the patient's body, wherein the calculating step utilizes a subset of the measurement data selected responsive to receiving a signal from the programming unit.

* * * * *